(12) United States Patent
Garrison et al.

(10) Patent No.: US 10,272,269 B2
(45) Date of Patent: Apr. 30, 2019

(54) DEVICES AND METHODS FOR ENDOLUMINAL DELIVERY OF EITHER FLUID OR ENERGY FOR DENERVATION

(71) Applicant: Silk Road Medical, Inc., Sunnyvale, CA (US)

(72) Inventors: Michi E. Garrison, Sunnyvale, CA (US); Richard M. Ruedy, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 1465 days.

(21) Appl. No.: 14/078,149

(22) Filed: Nov. 12, 2013

(65) Prior Publication Data

US 2014/0135661 A1 May 15, 2014

Related U.S. Application Data

(60) Provisional application No. 61/725,871, filed on Nov. 13, 2012.

(51) Int. Cl.
| | |
|---|---|
| *A61B 17/32* | (2006.01) |
| *A61N 7/00* | (2006.01) |
| *A61N 7/02* | (2006.01) |
| *A61B 18/14* | (2006.01) |
| *A61B 17/34* | (2006.01) |

(Continued)

(52) U.S. Cl.
CPC ............ *A61N 7/00* (2013.01); *A61B 17/3478* (2013.01); *A61B 18/1492* (2013.01); *A61N 7/022* (2013.01); *A61B 2017/22054* (2013.01); *A61B 2017/22067* (2013.01); *A61B 2017/22082* (2013.01); *A61B 2018/00291* (2013.01); *A61B 2018/00404* (2013.01); *A61B 2018/00434* (2013.01); *A61B 2018/00511* (2013.01);

(Continued)

(58) Field of Classification Search
CPC .......... A61B 2017/348; A61B 18/1492; A61B 5/6839; A61B 5/6853; A61B 5/6882; A61N 1/0558; A61N 1/05
See application file for complete search history.

(56) References Cited

U.S. PATENT DOCUMENTS

| 6,364,876 B1 * | 4/2002 | Erb .................... A61B 18/14 |
| | | 600/387 |
| 6,413,235 B1 | 7/2002 | Parodi |

(Continued)

OTHER PUBLICATIONS

Henry et al. (1999) "Carotid stenting with cerebral protection: First clinical experience using the PercuSurge GuardWire System" *J. Endovasc. Surg.* 6:321-331.

(Continued)

*Primary Examiner* — Alyssa M Alter
(74) *Attorney, Agent, or Firm* — Mintz Levin Cohn Ferris Globsky and Popeo, P.C.

(57) ABSTRACT

Described herein are methods and devices for selectively applying either fluids (e.g., anesthetics, nerve-blockers, etc.) or energy, such as radiofrequency or ultrasound energy, to a target tissue from within a blood vessel while minimizing the amount of fluid or energy applied to non-target tissue. The catheters described herein may include an elongate body, a directional injector, and one or more holdfasts for securing the catheter. In addition, catheters can include energy applying features for delivering energy to the target tissue.

15 Claims, 19 Drawing Sheets

(51) Int. Cl.
*A61B 18/00* (2006.01)
*A61B 17/22* (2006.01)

(52) U.S. Cl.
CPC ............... *A61B 2018/00577* (2013.01); *A61B 2218/002* (2013.01)

(56) References Cited

U.S. PATENT DOCUMENTS

| | | | |
|---|---|---|---|
| 6,423,032 B2 | 7/2002 | Parodi | |
| 6,595,953 B1 * | 7/2003 | Coppi | A61B 17/12045 604/93.01 |
| 6,837,881 B1 | 1/2005 | Barbut | |
| 7,083,594 B2 | 8/2006 | Coppi | |
| 7,879,011 B2 | 2/2011 | Chang | |
| 8,150,520 B2 | 4/2012 | Demarais et al. | |
| 2005/0154349 A1 | 7/2005 | Renz et al. | |
| 2006/0041277 A1 * | 2/2006 | Deem | A61N 1/0551 607/3 |
| 2006/0184048 A1 * | 8/2006 | Saadat | A61B 1/0008 600/478 |
| 2007/0287886 A1 * | 12/2007 | Saadat | A61B 1/0008 600/115 |
| 2010/0168731 A1 | 7/2010 | Wu et al. | |
| 2012/0232409 A1 | 9/2012 | Stahmann et al. | |
| 2012/0265198 A1 | 10/2012 | Crow et al. | |

OTHER PUBLICATIONS

U.S. Appl. No. 12/645,179, filed Dec. 22, 2009, US 2010-0217276.
U.S. Appl. No. 13/961,746, filed Aug. 7, 2013, US 2014-0046346.
U.S. Appl. No. 14/227,585, filed Mar. 27, 2014, US 2014-0296769.
U.S. Appl. No. 14/710,400, filed May, 12, 2015, US 2015-0327843.
U.S. Appl. No. 14/935,252, filed Nov. 6, 2015, US 2016-0128688.
U.S. Appl. No. 15/049,637, filed Feb. 22, 2016, US 2016-0242764.
U.S. Appl. No. 15/093,406, filed Apr. 7, 2016, US 2016-0296690.
U.S. Appl. No. 15/141,060, filed Apr. 28, 2016, US 2016-0317288.
U.S. Appl. No. 15/168,786, filed May, 31, 2016, US 2016-0271315.
U.S. Appl. No. 15/399,638, filed Jan. 5, 2017, US 2017-0209260.
U.S. Appl. No. 15/489,055, filed Apr. 17, 2017, US 2017-0312491.
U.S. Appl. No. 15/601,587, filed May 22, 2017, US 2017-0354523.
U.S. Appl. No. 15/606,381, filed May 26, 2017, US 2017-0354803.
U.S. Appl. No. 15/613,891, filed Jun. 5, 2017, US 2017-0361072.
U.S. Appl. No. 15/613,921, filed Jun. 5, 2017, US 2017-0368296.
U.S. Appl. No. 15/641,966, filed Jul. 5, 2017, US 2017-0296798.

* cited by examiner

DEVICES AND METHODS FOR ENDOLUMINAL DELIVERY OF EITHER FLUID OR ENERGY FOR DENERVATION

REFERENCE TO PRIORITY DOCUMENT

This application is related to and claims the benefit of priority under 35 U.S.C. 119(e) of U.S. Provisional Application Ser. No. 61/725,871, titled, "Endoluminal Delivery of Either Fluid or Energy for Denervation," filed Nov. 13, 2012. Priority of the filing date of Nov. 13, 2012 is hereby claimed, and the disclosure of the provisional patent application is hereby incorporated by reference in its entirety.

BACKGROUND

Minimally invasive surgeries (e.g., percutaneous surgeries) account for an increasing number of medical procedures. These surgeries may result in less patient trauma and may yield a significant cost savings as a result of shorter hospitalization times and reduced therapy requirements, such as compared to open surgery. Percutaneous procedures can include endoscopic and catheter-based procedures, such as angioplasty (e.g., balloon angioplasty), stent delivery, and tissue ablation. In many of these procedures, pain, and even tissue damage, can be reduced or eliminated by targeting delivery of anesthesia to the nerves or other tissues adjacent to the vessel in which the procedure is taking place.

Examples of two treatments that could benefit from the controlled application of anesthetic to specific tissues include angioplasty and tissue ablation. For example, carotid angioplasty and stenting can result in stimulation of the carotid body, since acutely stretching or manipulating the carotid artery (which commonly occurs during angioplasty of this region) can stimulate the carotid body, which in turn can cause either bradycardia or hypotension. Patients with severe coronary artery disease or aortic stenosis may suffer concomitant cardiac arrest. Stent placement can also cause prolonged distention of the carotid artery resulting in continuous stimulation of the carotid sinus body, which may require treatment with vasopressor medications and require observation in an intensive care setting.

Similarly, the treatment of tissue within a vessel by ablation (e.g., using an ablation catheter), may deleteriously effect nearby tissue structures. Ablation of tissue from within the vessel lumen can heat even non-target tissue due to thermal diffusion from the application of energy (e.g., electrical energy). This heat may cause pain or trauma. The use anesthesia, particularly tumescent anesthesia, is one method of reducing the negative effects of endoluminal ablation. Tumescent anesthesia typically involves providing local anesthesia to a surgical site using dilute local anesthetic solution to both numb and "inflate" the tissue around the target ablation zone.

Another treatment that can benefit from minimally invasive surgery (e.g., percutaneous surgery) includes denervation of one or more nerve systems of a patient. Some studies have shown that denervation can be associated with improved physiological conditions in some patients. For example, denervation of at least a part of the renal sympathetic nervous system (SNS) can assist in improving hypertension. In addition, the carotid body can also play an important part in regulating hypertension and some studies have shown that altering the carotid body, such as altering either the sympathetic nerves or baroreceptors of the carotid body, can result in improved physiological results.

Hypertension can be a deadly disease when left untreated and is suffered by a growing number of people. Some studies have shown that sympathetic nerves, such as the renal SNS that runs through the adventitia surrounding renal arteries, can play a significant role in systemic hypertension. It is understood that hyperactivity of these nerves can cause renal hypertension. In addition, the carotid body, which is comprised of a group of chemoreceptors and baroreceptors located near the carotid artery bifurcation, can also play a significant role in hypertension. Hypertension can be treated with various drugs, such as antihypertensives, but recipients can experience a range of side effects, including increased risk of new-onset diabetes.

SUMMARY

Disclosed herein are devices and methods related selectively applying either fluids or various forms of energy to one or more target areas within a body of a patient. Some device embodiments disclosed herein include a catheter device including an elongate body having a distal end and a proximal end, and a holdfast positioned adjacent the distal end of the elongate body. In addition, the holdfast can be configured to anchor the catheter device within a vessel of a body. Additionally, the catheter device can include an energy providing feature positioned adjacent the distal end of the elongate body and configured to deliver energy to a target area.

Some method embodiments disclosed herein can include inserting at least a part of a catheter device into a vessel body, wherein the catheter device includes an elongate body having a distal end and a proximal end. In addition, the catheter device can further include a holdfast positioned adjacent the distal end of the elongate body that can be configured to anchor the catheter device within a vessel of a body. Additionally, the catheter device can include an energy providing feature positioned adjacent the distal end of the elongate body that can be configured to deliver energy to a target area. The method can further include positioning the energy providing feature of the catheter device within the vessel body and adjacent the target area, and anchoring the catheter device with the holdfast. In addition, the method can include delivering energy from the energy feature to the target area.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1A:
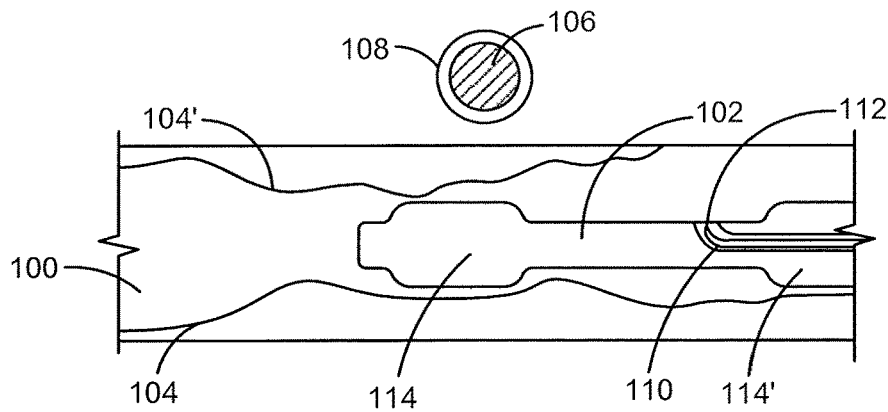
FIGS. 1A-1D illustrate one variation of the methods and devices described herein.

A minimally invasive solution is described herein for at least reducing the activity of nerves surrounding the renal artery and comprising the carotid body. Some minimally invasive solutions can include locating and delivering neurotoxic or nerve-blocking agents into the tissue surrounding the nerves, such as in the adventitia. Alternatively or in addition, various forms of energy can be applied to a target location, which can include at least one of the carotid arteries, the carotid body, renal veins or renal arteries. For example, either radiofrequency (RF) or ultrasonic energy can be applied to a target location within the body in order to assist in altering nerve functioning of one or more nerves, such as denervating the renal SNS, in order to improve physiological conditions (e.g., hypertension, heart failure, diabetes, renal failure, etc.) of a patient.

Many catheters do not allow precise stability and control, and may have problems controlling the amount and positioning of material or energy delivered in the body. Stability of the catheter can be important when it is desirable to apply either a fluid (e.g., a fluid containing an anesthetic or nerve-blocker) or energy (e.g., RF energy or ultrasonic energy) to a precise location outside of the vessel lumen. For example, movement of the catheter during delivery of fluid or energy can lead to damage of the vessel or extravascular structures. This may be particularly true when the wall of the vessel is difficult to penetrate (e.g., because of plaque such as arterial plaques, etc.), or is irregularly shaped. In addition, movement of the catheter during delivery of energy within a vessel can result in unwanted, including potentially harmful, tissue damage.

Described herein are methods and devices for selectively applying fluids (including anesthetics) to a target tissue from within a blood vessel while minimizing the amount of fluid applied to non-target tissue. The injection catheter devices (or components of these devices) may generally be used to perform the methods for selectively applying fluids to target tissues.

The methods of selectively applying anesthetic to a target structure generally involve positioning the injection catheter within the body vessel near the target structure, anchoring the injection catheter to stabilize it and to provide support or leverage for an extendable injector, then extending the injector and applying a fluid from the injection catheter to the target structure.

In addition, described herein are methods and devices for selectively applying either fluids or various forms of energy (e.g., RF, ultrasonic, etc.) to one or more target locations within a body of a patient in order to temporarily or permanently alter the functioning of one or more nerves, such as denervation. For example, target locations within the body can include at least a part of the renal SNS, a carotid body or any tissue or nerve which can assist in causing or facilitating physiological ailments, such as hypertension. In addition, the methods and devices described herein can selectively apply either fluids or various forms of energy to a target location from within a blood vessel and minimize the amount of either fluid or energy applied to non-target locations. In addition, methods and devices herein can selectively apply either fluids or various forms of energy directly to the target location.

Various catheter devices, including their components, can be used to perform the methods for selectively applying either fluids or various forms of energy to target locations within the patient. Some methods of selectively applying either fluids or various forms of energy to target locations can include positioning the catheter within the body vessel near the target structure, anchoring the catheter to stabilize and securing the catheter to the vessel wall. Fluid or energy can then be delivered from the catheter to the target structure.

Some embodiments of the catheter device can be configured to deliver one or more types of drugs or substances to a target location in the body to assist in altering the functioning of one or more nerves, such as denervation. In some method embodiments, the drug or substances can be delivered by positioning the injection catheter (also referred to herein as simply a "catheter") within the body vessel near the target location. The target location can include at least one target tissue area, such as at least a part of the renal SNS or carotid body. Once an injector of the catheter is positioned near the target location, the catheter can be anchored within the vessel in order to stabilize the catheter and provide support or leverage for an extendable injector to deliver the drugs to the target location. The injector can then be deployed or extend from the catheter and inject the drug into the target location, such as at or near the target tissue in order to assist in denervating one or more nerves.

One or more of a variety of drugs can be injected into the target location and can include, for example, Guanethidine, which is often supplied in the sulfate form, guanethidine sulfate or guanethidine monosulfate (CAS 645-43-2) with chemical name Guanidine, [2-(hexahydro-1(2H)-azocinyl) ethyl]-, sulfate (1:1). Guanethidine has been marketed under the trade name Ismelin. Alternatively or in addition, 10% phenol in ethynol or absolute ethenol can be injected into the target location.

Other agents have been shown to create partial or complete sympathectomy as well. These include immunosympathectomy agent anti-nerve growth factor (anti-NGF); auto-immune sympathectomy agents anti-dopamine beta-hydroxylase (anti-DβH) and anti-acetylcholinesterase (anti-AChe); chemical sympathectomy agents 6-hydroxyldopamine (6-OHDA), bretylium tosylate, guanacline, and N-(2-chloroethyl)-N-ethyl-2-bromobenzylamine (DSP4); and immunotoxin sympathectomy agents OX7-SAP, 192-SAP, anti-dopamine beta-hydroxylase saporin (DBH-SAP), and anti-dopamine beta-hydroxylase immunotoxin (DHIT). Phenol and ethanol have also been used to produce chemical sympathectomy and are also useful in the methods described herein. Other sympatholytic agents can include alpha-2-agonists such as clonidine, guanfacine, methyldopa, guanidine derivatives like betanidine, guanethidine, guanoxan, debrisoquine, guanoclor, guanazodine, guanoxabenz, guancydine, guanadrel and the like; imadazoline receptor agonists such as moxonidine, relmenidine and the like; ganglion-blocking or nicotinic antagonists such as mecamylamine, trimethaphan and the like; MAOI inhibitors such as pargyline and the like; adrenergic uptake inhibitors such as rescinnamine, reserpine and the like; tyrosine hydroxylase inhibitors such as metirosine and the like; alpha-1 blockers such as prazosin, indoramin, trimazosin, doxazosin, urapidil and the like; non-selective alpha blockers such as phentolamine and the like; serotonin antagonists such as ketanserin and the like; and endothelin antagonists such as bosentan, ambrisentan, sitaxentan, and the like; and sclerotherapeutic agents such as quinacrine, chloroquine, sodium tetradecyl sulfate, ethanolamine oleate, sodium morrhuate, polidocanol, phenol, ethanol, or hypertonic solutions At least some of the injection catheters described herein can have an elongate body, a directional injector, and a holdfast to secure the injection catheter within the vessel. The combination of these features can result in a device that can selectively and precisely apply fluid to a target site outside of the vessel lumen in which the injection catheter is positioned. As described more fully below, these injection catheters can remain stable even when manipulating the injector to penetrate tissue between the injection catheter and the target tissue. Furthermore, these injection catheters may control the way that fluid is applied near or on the target tissue to prevent damage to the target tissue or more proximal tissues.

Although many of the examples provided herein refer to the application of anesthetics or fluids containing anesthetics, any appropriate fluid may be used, such as with or without anesthetics. For example, fluids may include saline, or solutions containing drug or therapeutics (e.g., proteins, enzymes, small molecules, antibody-based therapeutics, nucleotide-based therapeutics, etc.). When anesthetics are used, any appropriate anesthetic may be used, including Benzocaine, Mepivacaine, Ropivacaine, Bupivacaine, Lidocaine, Prilocaine, Procaine, Chloroprocaine, etc.

In addition, drugs or substances for assisting in temporarily or permanently altering the nerve functioning of one or more nerves, such as denervation, can be used with any of the injection catheters, or catheters, described herein. Additional substances can be included with the drugs, such as hydrogels, for providing various drug delivery and drug dispersion characteristics within the target location.

Some catheter embodiments described herein are configured to deliver various forms of energy and can include one or more of an elongate body and a holdfast to secure the catheter within the vessel. In addition, the catheter may or may not include an extendable injector for delivering fluid to a target location outside of the vessel lumen. Additionally, the catheter can include components for assisting in delivering various forms of energy to target locations within the body. For example, catheters can be configured for delivering either RF energy or ultrasound energy from within the vessel to the target location, such as in order to perform denervation. Catheters can control the way that either RF energy or ultrasound energy is applied near or on the target location in order to prevent damage to the target tissue or more proximal tissues.

For example, a catheter device embodiment can be configured to include one or more RF electrodes for assisting in the delivery of RF energy to a target location within the body. In some method embodiments, the RF energy can be delivered to the target location, such as at or near the renal SNS or carotid body, by positioning the catheter within the body vessel near the target location. Once the RF electrodes of the catheter are positioned near the target location, the catheter can be anchored within the vessel in order to stabilize and position the catheter and allow the electrodes to safely and effectively deliver RF energy to the target location. The RF energy can cause thermal destruction of the neural tissue, which can result in denervation of at least a part of the SNS.

The electrodes can be placed in direct contact with tissue, such as the vessel wall or the target tissue during the delivery of RF energy to the target location. Alternatively or in addition, the electrodes can be positioned such that they are not in contact with tissue during delivery of RF energy to the target location. Moreover, electrodes can be positioned relative to each other and the target location in a variety of configurations. For example, the electrodes can be positioned relative to each other in order to deliver RF energy within a defined target location area. By way of further example, the position of the electrodes relative to each other and the target location can be changed, including after the catheter has been inserted into a vessel body, in order to change the delivery area of the RF energy from the electrodes.

Some embodiments of the catheter device can be configured to include one or more transducers and acoustic elements for assisting in the delivery of ultrasound energy to a target location within the body. In some method embodiments, the ultrasound energy can be delivered to the target location, such as at or near the renal SNS or carotid body, by positioning the catheter within the body vessel near the target location. Once the transducers and acoustic elements of the catheter are positioned near the target location, the catheter can be anchored within the vessel in order to stabilize and position the catheter for allowing the transducers and acoustic elements to safely and effectively deliver ultrasound energy to the target location.

The transducers and acoustic elements can be placed in direct contact with tissue, such as the vessel wall or the target tissue, during the delivery of ultrasound energy to the target location. Alternatively or in addition, the transducers and acoustic elements can be positioned such that they are not in contact with tissue during delivery of ultrasound energy to the target location. Moreover, transducers and acoustic elements can be positioned relative to each other and the target location in a variety of configurations. For example, the transducers and acoustic elements can be positioned relative to the target location in order to deliver ultrasound energy within a defined target location area. By way of further example, the position of the transducers and acoustic elements relative to each other and the target location can be changed, including after the catheter has been inserted into a vessel body, in order to change the delivery area of the ultrasound energy from the transducers and acoustic elements.

As described above, the method of selectively applying fluid to a target structure selectively delivers fluid from an injection catheter within a body vessel to the target tissue without substantially applying fluid to non-target structures. This can be accomplished, for example, by inserting an injection catheter into a body vessel, positioning the injection catheter within the body vessel near the target structure, anchoring the injection catheter before extending the directional injector to selectively deliver fluid to the target structure, and applying fluid from the injection catheter to the target structure. Any appropriate injection catheters may be used, particularly the injection catheter described herein.

In addition, some method embodiments can include selectively applying fluid to a target location, such as tissue surrounding one or more nerves, in order to assist with denervation of the one or more nerves. As discussed above, denervation of some nerves that assist in regulating blood flow, such as the renal SNS and carotid body, can assist in improving hypertension in a patient. Therefore, the target location can include the adventitia of the renal artery where at least a part of the renal SNS can be found. The fluid can be delivered to the target location such that it can assist in denervation of the desired nerves without applying a substantial amount of fluid to non-target locations. This can be accomplished, for example, by inserting an injection catheter into a body vessel, positioning the injection catheter within the body vessel near the target location, anchoring the injection catheter before extending the directional injector to selectively deliver fluid to the target location, and delivering fluid from the injection catheter to the target location within the body. Any appropriate injection catheters may be used, particularly the injection catheter described herein.

The injection catheter may be inserted into any appropriate opening into a body vessel or lumen. For example, the injection catheter may be inserted as part of any percutaneous procedure (e.g., through the subject's skin into the vasculature) so that the vessel is a blood vessel (e.g., artery or vein), or into any other appropriate vessel in the body. For example, the injection catheter may be inserted into a lymphatic vessel, the intestinal tract, etc. Insertion and/or placement of the injection catheter may be manual (e.g., it may be advanced by hand), assisted, or automatically (e.g., robotically). The injection catheter may be used with additional devices to assist in placement and positioning. For example, insertion may involve the use of a sheath or guidewire. Thus, a flexible guidewire may be advanced to a location in the body, and the injection catheter may be advanced along the guidewire through the body until correct positioning is reached.

In addition, various forms of therapy, such as either drug delivery or various forms of energy delivery, can be delivered to the carotid artery or carotid body transcervically via an access site in the common carotid artery, rather than transfemorally via an access site in the femoral artery. A catheter designed for transcervical delivery can be shorter than that designed for transfemoral delivery, as the target anatomy is within 5-15 cm from the access site. A transcervical catheter length could be approximately half that of a transfemoral catheter length, for example 40 cm to 80 cm in length, as opposed to 100 cm to 160 cm in length which can provide some benefits. For example, shorter catheter lengths can require lower fluid pressures necessary for the delivery of fluids to the target location. The need for shorter catheter lengths can also result in faster procedure times, such as for locating and positioning the catheter prior to and during delivery of drugs or energy (e.g., RF or ultrasound).

Once the injection catheter (or "catheter") is inserted into the body vessel, it is advanced to a position in the body vessel adjacent or near the target tissue. At any time during the procedure one or more sensing techniques may be used to assist the practitioner (e.g., doctor, nurse, etc.) in positioning and controlling the injection catheter. For example, the catheter may include one or more sensors (e.g., cameras, ultrasound transducers, etc.) on it to detect the position in the subject's body, or to allow for an external device to locate the injection catheter. The catheter and the subject's body may also (or alternatively) be visualized using any appropriate visualization technique. For example, the subject's body may be visualized using a fluoroscope, an ultrasound, etc. A "subject" may be anyone in need of treatment, including medical patients. Subjects may include humans and animals.

To aid in visualizing the position of the injection catheter within the subject's body, any appropriate contrast agent or marker may be used. The contrast material may be matched to the type of imaging modality used (e.g., radiopaque materials may be used, fluorescent dyes, etc.). In addition, fluid delivered by the injection catheter may also contain a contrast agent or marker, to allow monitoring of the delivery of the fluid within the subject's body. For example, a contrast agent may be used with the anesthetic solution. Thus, the practitioner can confirm that the material has been correctly applied. In some variations, a small amount of fluid (even without anesthesia) may be applied to confirm that the injection catheter has been correctly positioned.

In some method embodiments, the injection catheter can be positioned near the target structure so that the injection catheter can access the target structure from within the lumen of the vessel by extending the injector. The step of positioning the injection catheter may include advancing, withdrawing and otherwise orienting the injection catheter. For example, the injection catheter may be advanced within the vessel, withdrawn from the vessel, rotated within the vessel, or moved laterally within the vessel. In some variations, the injection catheter can be manipulated by controlling the proximal end of the injection catheter.

Manipulation of the injection catheter may initially involve a "rough" positioning to place the catheter near the target site within the subject's body. In some variations, once the catheter has been roughly positioned within the proximity of the target tissue, it can be more accurately positioned by fine positioning after it has been secured into position within the vessel by a holdfast. Positioning the catheter within the vessel may also be done iteratively. For example, the catheter may be positioned, secured into place with the holdfast, and then unsecured and moved to reposition the catheter.

Positioning the catheter may mean positioning the injector (or injectors) of the injection catheter so that the injector can access the target tissue. For example, in variations of the injection catheter having an elongate injector that extends from an exit port or recess in the body of the catheter, the catheter may be positioned so that the exit port for the injector is adjacent to the target tissue, which can allow the injector to be extended from the injection catheter and into the target tissue. In some variations of the injection catheter, the rough positioning of the injection catheter is adequate for this purpose. In other variations, the injection catheter may include a fine positioning region (or an injector positioning region) that may be controllably manipulated to allow limited positioning of the injector even after the injection catheter has been secured into position by a holdfast.

An injector positioning region may be a region of the injection catheter (e.g., encompassing the exit port) that can controllably slide (proximally and/or distally) over a limited distance on the injection catheter, and may also rotate (e.g., around the circumference of the injection catheter). The movement of this region may be controllable by the user from the proximal end of the catheter. In some variations, the angle that the injector exits the injection catheter may be controlled to "aim" the tip of the injector within a set radius (e.g., within about ±20° from a direction normal to the long axis of the injection catheter). Aiming the injector in this way may be accomplished by changing the position of the exit port with respect to the rest of the injection catheter, and/or changing the angle of a deflection plate (described further below) which changes the trajectory of some types of injectors so that they may exit the injection catheter from a lumen within the injection catheter.

Once the injection catheter is at least roughly positioned, it is anchored or secured into position within the vessel, to prevent substantial movement of the injection catheter with respect to the vessel. Any appropriate holdfast (or combination of holdfasts) may be used, including inflatable balloons, suction ports, braces, clamps, adhesives, rigid or rigidifiable members, expandable scaffolds, magnetic locks, etc. The holdfast can prevent the catheter from moving due to gross movements (e.g., flow of fluids within or around the catheter, mechanical motion of the subject, etc.), which can change the position of the injector with respect to the target tissue. The holdfast may also prevent changes in the relative position of the injector and the target tissue as fluid (e.g., anesthetic, nerve-blocking agent, etc.) is applied. In variations of the injection catheter having a fine positioning control, an additional "lock" may be provide to secure the fine controls in a fixed position once the injector has been correctly positioned so the injector can be extended and contact the target tissue.

The target tissue, or target area, may be any appropriate tissue or body region as described above. In particular, the target tissue, or target area, is a tissue that is located adjacent to a vessel which may receive the injection catheter and is within the extension range of the injector (particularly the fluid delivery section of the injector). For example, the target area may comprise a nerve, a nerve system, tissue surrounding a nerve, or a sheath around a nerve. In the variation descried in Example 1, below, the target area can be the region surrounding the carotid body. In some variations, the target area may be a tissue layer or fascia, such as the layers between vessels or other regions of body organs. For example, it may be desirable to inject anesthetic specifically within such a layer before performing a surgical procedure (e.g., ablation) on the tissue area or adjacent tissue.

The injection catheter can be anchored before extending the injector because the movement of the injection catheter as it is being extended may otherwise disrupt the position of the injection catheter as the injector pushes against the tissue. This can be particularly problematic when extending the injection catheter into resilient tissues that resist penetration, or tissues having plaques (e.g., atherosclerotic plaques). Anchoring the injection catheter into position within the vessel can provide leverage so that the injector can apply force to penetrate the tissue and reach the target, without substantially changing the position of the injection catheter. In some variations, the holdfast may itself act as a support or brace for the injector.

The user can extend the injector from the body of the injection catheter. In some variations, the injector is contained within the body of the injection catheter, and exits from an exit port on the side or the end of the injection catheter. The injector may be manually or automatically extended. The injector and injection catheter may also be structured to limit the distance and/or rate that the injector extends. Once the injector is extended and positioned in, near, or on the target tissue, fluid may be applied. In some variations, the fluid applied is a local anesthetic solution. Fluid is typically applied by supplying pressure (e.g., from a syringe, pump, etc.) to the proximal end of the catheter, pushing fluid (which may be preloaded into the injector before positioning) from the injector into the tissue. The amount of pressure used to apply the fluid may be regulated at the proximal end, or the injector itself may include a structure (e.g., a filter, buffer, etc.) to limit the force which fluid exits the injector.

Any of the injectors described herein may be directional injectors, as described further below. In general, a directional injector applies fluid in a selected direction. For example, the directional injector may apply fluid in a direction that is perpendicular to the direction of extension of the injector or opposite the direction of extension of the applicator. In some variations, the directional injector applies fluid from a fluid delivery section that is located on the side of the injector. The injector may be adapted to apply fluid in a plane (e.g. parallel to the injection catheter).

Alternatively or in addition to providing injection of one or more fluids to a target area or structure within the body, the catheter can be configured to provide various forms of energy (e.g., RF energy, ultrasound energy, etc) to one or more target locations within the body. In addition, some method embodiments can include selectively applying various forms of energy to a target area, such as tissue surrounding one or more nerves, in order to assist with altering the functioning of the nerves, including denervation. As discussed above, denervation of some nerves that assist in regulating blood flow, such as the renal nerves, renal SNS and carotid body, can assist in treating hypertension.

The various forms of energy can be delivered to the target location or structure such that it can assist in either temporarily or permanently altering the functioning of one or more nerves, including denervation, without substantially disrupting non-target locations. This can be accomplished, for example, by inserting a catheter into a body vessel, positioning the catheter within the body vessel near the target area, anchoring the catheter before delivering the energy to the target area, powering the energy providing features (e.g., electrode, transducer, acoustic element) to deliver energy to the target location, and delivering energy (e.g., RF energy, ultrasound energy, etc.) from the injection catheter to the target location within the body. Any appropriate catheter may be used, particularly the injection catheter or catheters described herein.

Similar to as described above, the catheter configured to apply energy to one or more target locations within the body can be inserted into any appropriate opening into a body vessel or lumen. For example, the catheter may be inserted as part of any percutaneous procedure (e.g., through the subject's skin into the vasculature) so that the vessel is a blood vessel (e.g., artery or vein), or into any other appropriate vessel in the body. For example, the catheter may be inserted into a lymph vessel, the intestinal tract, etc. Insertion and/or placement of the catheter may be manual (e.g., it may be advanced by hand), assisted, or automatically (e.g., robotically). The catheter may be used with additional devices to assist in placement and positioning. For example, insertion may involve the use of a sheath or guidewire. Thus, a flexible guidewire may be advanced to a location in the body, and the catheter may be advanced along the guidewire through the body until it reaches the correct position.

Once the catheter is inserted into the body vessel, it is advanced to a position in the vessel adjacent or near the target area, or target location. For example, the catheter can be positioned in the renal artery in order to deliver energy to the renal nerves, or renal SNS, extending through the adventitia surrounding the renal artery. At any time during the procedure one or more sensing techniques may be used to assist the practitioner (e.g., doctor, nurse, etc.) in positioning and controlling the catheter. For example, the catheter may include one or more sensors (e.g., cameras, ultrasound transducers, etc.) on it to detect the position in the subject's body, or to allow for an external device to locate the catheter. The catheter and the subject's body may also (or alternatively) be visualized using any appropriate visualization technique. For example, the subject's body may be visualized using fluoroscope, ultrasound, etc.

To aid in visualizing the position of the catheter within the subject's body, any appropriate contrast agent or marker may be used. The contrast material may be matched to the type of imaging modality used (e.g., radiopaque materials may be used, fluorescent dyes, etc.). In addition, fluid delivered by the catheter may also contain a contrast agent or maker, to allow monitoring of the delivery of the fluid within the subject's body. For example, a contrast agent may be used with the anesthetic solution. The catheter can be positioned near the target location so that the catheter can apply energy to the target location, such as an area which includes renal nerves, renal SNS, or the carotid body. The step of positioning the catheter may include advancing, withdrawing and otherwise orienting the catheter. For example, the catheter may be advanced within the vessel, withdrawn from the vessel, rotated within the vessel, or moved laterally within the vessel. In some variations, the catheter is manipulated by controlling the proximal end of the injection catheter.

Manipulation of the catheter can initially involve a "rough" positioning to place the catheter near the target area, or target location, within the subject's body. In some variations, once the catheter has been roughly positioned within the proximity of the target area, it can be more accurately positioned by fine positioning after it has been secured into position within the vessel by a holdfast. Positioning the catheter within the vessel may also be done iteratively. For example, the catheter may be positioned and secured into place with the holdfast, and then unsecured and moved to reposition the catheter.

The step of positioning the catheter can include positioning the one or more energy applying features which assist in delivering energy to the target location. For example, a catheter configured to deliver RF energy to the target area can include one or more electrodes. The electrodes can be activated to deliver an amount of RF energy to the target area from within the vessel. In some method and device embodiments, the catheter is configured to place the electrodes against tissue, such as the vessel walls, during application of RF energy to a target location. Alternatively or in addition, the catheter can be configured to position the electrodes away from tissue, such as positioned within the vessel and away from the vessel wall, during application of RF energy to the target location.

When applying RF energy to a target location, a pulsed electric field (PEF) can be applied to the target location in order to achieve neuromodulation, such as denervation. For example, the catheter can apply a PEF to cause either electroporation or electrofusion in neural fibers, such as neural fibers of renal SNS or the carotid body. Any suitable electrical signal or field parameter can be used in order to achieve neuromodulation, including denervation, of desired nerves. In addition, a variety of electrical signals or field parameters can be used to create various electroporative and electrofusion effects. For example, pulsed electric fields can be applied in a variety of ways in order to cause a variety of alterations in nerve functioning, such as reduce or eliminate the ability of nerves to conduct electrical impulses.

Alternatively or in addition the catheter can be configured to deliver ultrasound energy to the target location. For example, a catheter configured to deliver ultrasound energy to the target location can include at least one transducer and acoustic element, or any number of features, which can assist in providing ultrasound energy to the target location within the body. In addition, the transducer and acoustic element can be activated to deliver an amount of ultrasound energy to the target location from within the vessel. In some method and device embodiments, the catheter can be configured to place the either the transducer or acoustic element against tissue, such as the vessel walls, during application of ultrasound energy to a target location. Alternatively or in addition, the catheter can be configured to position the transducer or acoustic element away from tissue, such as positioned within the vessel and away from the vessel wall, during application of ultrasound energy to the target location.

When applying ultrasound energy to a target location one or more functions or parameters can be defined in order to control the amount of ultrasound energy and area of tissue affected by the ultrasound energy. For example, some parameters can include at least the impedance of the acoustic element, temperature controls, impulse excitation, catheter positioning, electric power applied to the transducer, voltage applied to the transducer, current applied to the transducer, frequency of ultrasound energy produced by the vibration of the acoustic element, intensity of ultrasound power, pulse duration of the acoustic energy, and focusing of the ultrasound energy. Any suitable function or parameter can be used in order to achieve various alterations in nerve functioning, including denervation, of one or more nerves.

In some method embodiments of applying energy to nerves, electrical signals through the nerves are reduced by damaging some neurons in the nerve bundle. Alternatively or in addition, electrical signals through the nerves are prevented from passing through the nerves by damaging the entire nerve bundle. Furthermore, any one of a variety of tissue can be altered or damaged by applying energy, such as RF or ultrasound energy, without departing from the scope of the present disclosure.

In some variations of the catheter, the rough positioning of the catheter is adequate for the purpose of delivering energy within the body. In other variations, the catheter may include a fine positioning region (or an energy positioning region) that may be controllably manipulated to allow limited positioning of the catheter, such as the energy delivering components or features (e.g., electrodes, transducer, acoustic element, etc.) even after the catheter has been secured into position by a holdfast.

Once the energy providing features of the catheter (e.g., electrode, transducer, acoustic element, etc.) is at least roughly positioned, the catheter is anchored or secured into position within the vessel in order to prevent substantial movement of the catheter with respect to the vessel. Any appropriate holdfast (or combination of holdfasts) may be used, including inflatable balloons, suction ports, braces, clamps, adhesives, rigid members, members which can transition into a rigid state, expandable scaffolds, magnetic locks, etc. In addition, any of the holdfast features described for any of the injection catheters or energy applying catheters can be incorporated in any catheter embodiments at least described herein.

Energy from the catheter can be applied to any number of target areas, or target locations, including any appropriate tissue or body region as described herein. In particular, the target location can include one or more nerves located adjacent to a vessel, such as the renal nerve, renal SNS or carotid body. In particular, applying energy to the target location can alter nerve functioning, including denervation, of one or more nerves which can affect a variety of physiological conditions, such as blood pressure.

The catheter can be anchored before applying energy to the target location in order to ensure at least the energy providing features of the catheter (e.g., electrode, transducer, acoustic element, etc.) are properly positioned during the application of energy to the target location. Anchoring the catheter into position within the vessel can ensure that the desired tissues, including nerves, are affected by the application of energy to the target location. In addition, proper positioning of the catheter, including the energy providing features, can reduce the amount of tissue damage, including tissue damage that is harmful to the patient. In some embodiments, any of the holdfasts can include one or more energy applying features (e.g., electrode, transducer, acoustic element, etc.).

In some embodiments, at least one energy providing feature (e.g., electrode, transducer, acoustic element, etc.) can be placed on an extending feature, such as the extending injector. This can allow at least one energy providing feature (e.g., electrode, transducer, acoustic element, etc.) to directly contact target tissue (e.g., adventitia, nerve bundle, etc.) while applying energy to the target location. In this configuration, the practitioner can extends the extending element having the energy providing feature from the body of the catheter. Once the extending element is extended and positioned in, near, or on the target tissue, either fluid or energy can be applied. In some variations, fluid can be applied at least one of before, during or after energy is applied to the target location.

Fluid is typically applied by supplying pressure (e.g., from a syringe, pump, etc.) to the proximal end of the catheter, pushing fluid (which may be preloaded into the injector before positioning) from the injector into the tissue. The amount of pressure used to apply the fluid may be regulated at the proximal end, or the injector itself may include a structure (e.g., a filter, buffer, etc.) to limit the force which fluid exits the injector. Any of the injectors described herein may be used to either provide fluid or energy to the target location without departing from the scope of the present disclosure.

FIG. 1 illustrates one variation of the method for selectively applying anesthetic to a target structure or area. In FIG. 1A, an injection catheter or catheter device 102 is located within the lumen of a vessel 100. The walls of the vessel are irregular 104, 104' (e.g., as might be found in an artery or other vessel). Adjacent to a portion of the vessel is a structure 106 surrounded by a sheath 108. The injection catheter 102 includes an injector 110 which can exit the injection catheter from an exit port 112. The injection catheter 102 can also include two holdfasts, here configured as inflatable balloons 114, 114' on either side of the exit port 112 for the injector 110.

Figure 1B:
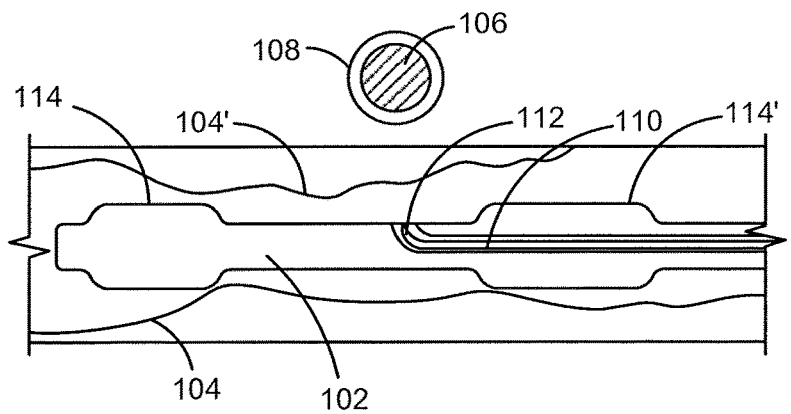

In the transition between FIG. 1A and FIG. 1B, the injection catheter 102 is positioned so that the exit port 112 for the injector 110 is positioned near the target area, which includes the structure 106 and sheath 108. In FIG. 1, the target area can also include an area adjacent to the sheath 108. For example, the structure 108 may be a nerve or nerve bundle (shown in cross-section) surrounded by a nerve sheath, as shown as sheath 108. In some variations, the target area may be the sheath 108 surrounding the structure 106.

Figure 1C:
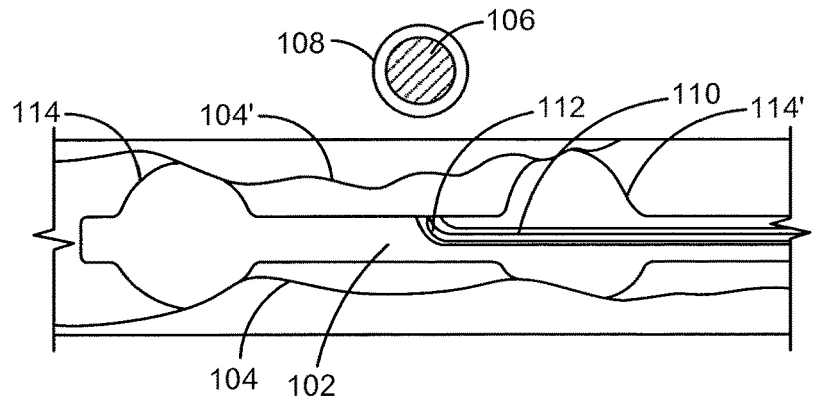

In FIG. 1B, the injection catheter 102 is shown positioned with respect to the target area. Once the injection catheter 102 has been positioned in the vessel, the holdfasts (as shown as balloons 114, 114') can be deployed, such as by inflating them until they secure the position of the injection catheter 102 within the vessel, as shown in FIG. 1C. The holdfast balloons 114, 114' can provide support against uneven walls of the vessel 104, 104' and prevent the vessel from moving.

The balloon-type holdfasts 114, 114' shown in FIGS. 1A-1D can expand radially around the injection catheter 102, and therefore may serve to center at least the surrounding portion of the injection catheter 102 within the center of the vessel lumen. The holdfast balloons 114, 114' (or other holdfast configurations) may also be asymmetrically positioned, so that they preferentially secure the injection catheter 102 to one side of the vessel (e.g., maintaining the shortest distance between the injector and the target tissue). Although two holdfast balloons 114, 114' are shown in FIGS. 1A-1D, it should be clear that no holdfast may be used, or that only one holdfast may be used, although in some variations more than one holdfast may be used (as shown). Furthermore, the position of the holdfast with respect to the exit port 112 for the injector 110 may also vary. In some variations, the holdfast may surround the exit port (and may include a passage for the injector). In some variations the holdfast (or holdfasts) can be located proximally or distally to the exit port for the injector.

Figure 1D:
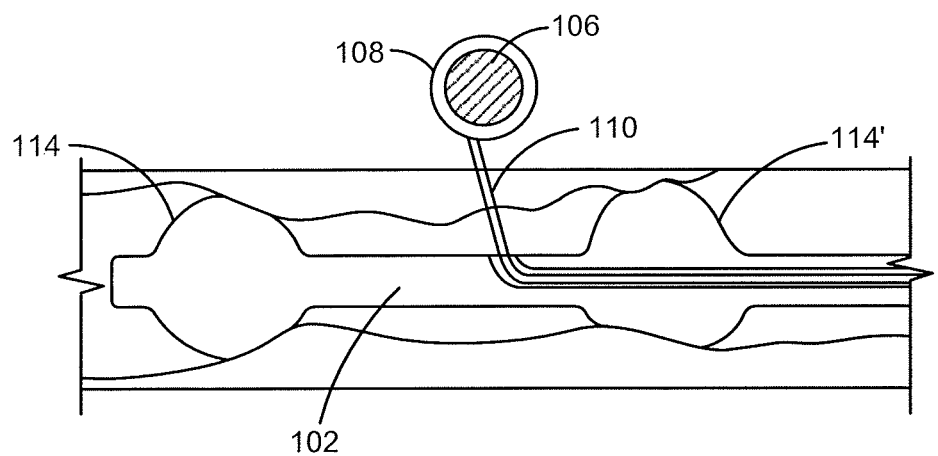
Figure 1E:
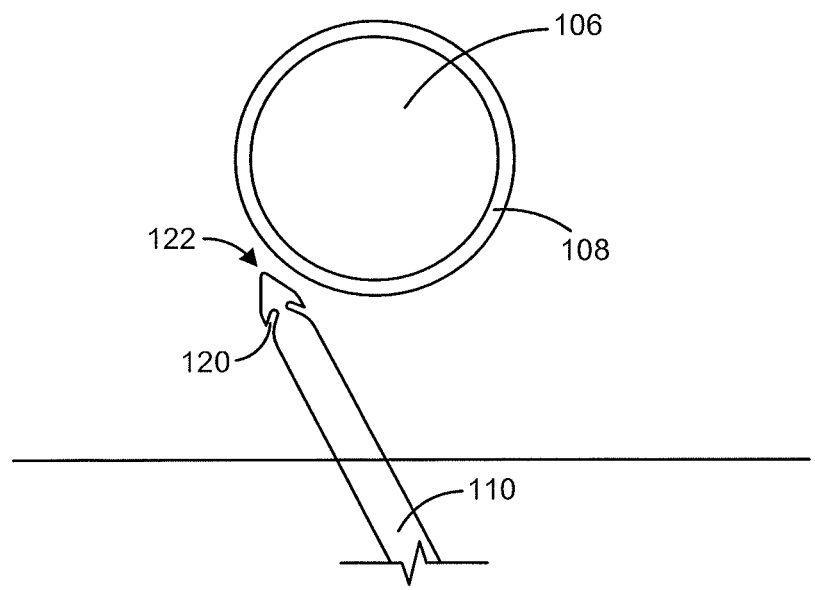
FIG. 1E shows an enlarged view of one portion of FIG. 1D.

As shown in FIGS. 1E and 1D, once the injection catheter 102 has been secured into position so that the exit port 112 of the injector 110 is located within reach of the target area, the injector 110 may be extended through the vessel toward the target area or structure, as shown in FIG. 1D. The injector 110 is extended from the injection catheter 102 (through the exit port) until it penetrates the vessel and approaches the target area, such as the sheath 108 or structure 106. The tip 122 of the injector 110 can be a tissue-penetrating region. As shown in FIG. 1E, the injector tip 122 can pointed, and can have a relatively small gauge (e.g., greater than a 22 gauge needle) so that it can readily penetrate the tissue. Proximal to the tip 122 along the injector 110 can be the fluid delivery section 120 of the injector 110. The fluid delivery section 120 can be positioned near or in the target area, such as the sheath 108 or structure 106, as shown in the enlarged view in FIG. 1E. Once the fluid delivery section 120 of the injector 120 is properly positioned, fluid (e.g., anesthetic) may be injected.

In some variations, the target area or target tissue can be a layer of tissue or fascia, or a region between structures. The injection catheter 102 and directional injectors 110 described herein may be used to specifically apply fluid between such tissue layers. Because the flow of fluid from the injector 110 may be specifically directed in a direction parallel with the tissue layer (e.g., by matching the fluid delivery section of the injector 110 with the direction of the tissue layer, and/or by using injectors that regulate the rate or force that fluid is applied).

In general, the injection catheters 102 described herein include an elongate body, a directional injector 110 that is extendable from the elongate body to penetrate tissue and deliver fluid in a direction that is different from the direction of tissue penetration, and a holdfast, such as the balloon holdfasts 114, 114', for securing the injection catheter 102 within the vessel and providing support and stability to the injector.

The injection catheter 102 has an elongate body with a distal and a proximal end. The elongate body generally has one or more lumens along at least a portion of its length (e.g., from the proximal end to at least the exit port for the injector. The elongate body may include at least one passage through which one or more injectors 110 are connected to a pressure or fluid source. In some variations, the elongate body includes additional passages, such as for a guidewire, endoscope, steering cable(s), or the like. The elongate body may be made of any appropriate material or materials, and may be flexible, jointed, stiffenable, or the like.

The injection catheter 102 may be steerable, and may be in a variety of lengths. For example, the injection catheter 102 may be approximately 3 feet to approximately 6 feet long (e.g., for percutaneous procedures entering through the femoral artery for procedures on target tissues located more distally). Additionally, the injection catheter 102 can have a relatively shorter length of approximately 4 inches to 3 feet, such as for more proximal entry into the body.

Figure 2A:
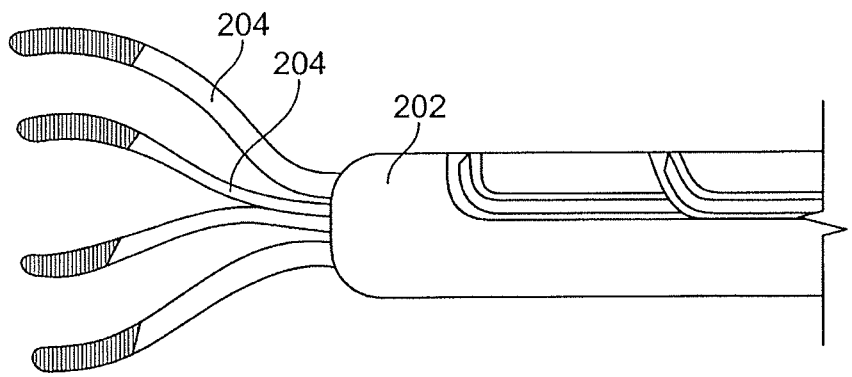
FIGS. 2A-2E show different variations of the injection catheter as described herein.

Injection catheters 102 may also include one or more holdfasts, as described briefly above. A holdfast may be any structure for securing the injection catheter 102 within the vessel lumen. Preferably, the holdfast can anchor the injection catheter within the injection lumen without damaging the lumen or causing injury to the subject. In general, the holdfast may releasably attach or secure the catheter within the vessel lumen. FIG. 2A shows some examples of different holdfasts that may be used with injection catheters. For example, in FIG. 2A, the holdfast comprises a plurality of "feet" 204 that project from the body of the injection catheter 202. These feet may be flexible (e.g., they may be made of a spring-like material) so that they can expand to contact the walls of the vessel when released from the body of the catheter. In the example shown in FIG. 2A, the feet of the holdfast are ejected from the distal end of the catheter, and expand outwards to contact the vessel as the feet are extended. The ends of the feet may be configured so that they do not puncture or harm the vessel walls. For example, the feet may be coated in a rubber or silicone. In some variations, the feet may be coated or treated with a material that readily adheres to the walls of the vessel.

Figure 2B:
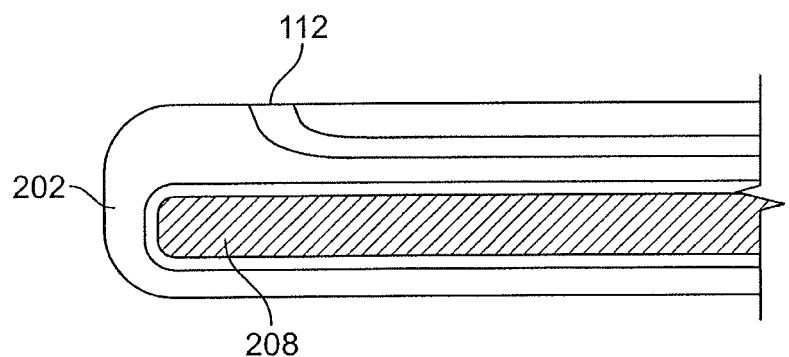

FIG. 2B shows another example of a holdfast, comprising a stiff rod 208 that locks the (otherwise flexible) catheter body into position, at least over the region near the exit port 112 for an injector (not shown). The rigid rod may provide structural support for the injector as it is extended from the injection catheter 202. In some variations, the injector is coupled to the body of the stiff rod 208, so that the rod provides support for injector (and may steer the injector) as it is extended from the injection catheter.

Figure 2C:
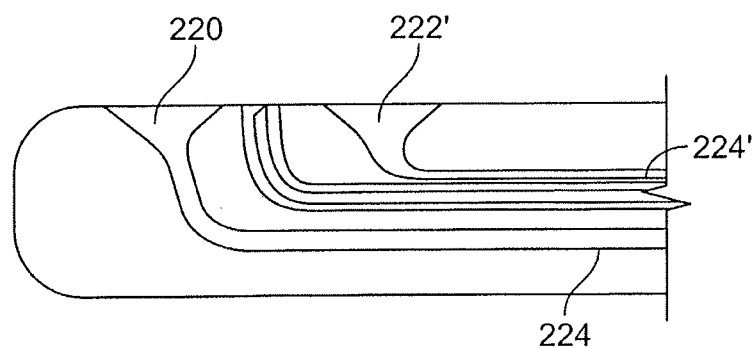

The holdfast shown in FIG. 2C is a vacuum-type holdfast having two vacuum ports 220, 222' that connect (via channels 224, 224') to a vacuum source. A vacuum may be applied through these ports so that when the injection catheter is brought near the vessel wall, the injection catheter will suck onto the wall of the vessel and be held securely.

The amount of vacuum may be controlled to prevent damage to the walls of the vessel. Additional variations of the holdfast may be used as well (including the balloon-type holdfasts shown in FIG. 1). As previously mentioned, the injection catheter may include multiple holdfasts which may be positioned in any appropriate way.

The injection catheter also includes one or more injectors, including directional injectors, for injecting fluid (e.g., anesthetic) to a target tissue. Injectors are extendable from the elongate body of the injection catheter. In some variations, the injectors extend from the side of a distal portion of the injection catheter; however they may also extend from the distal end, or from more proximal locations. The injector typically comprises a tissue-penetrating section at the distal end of the injector and a fluid delivery section located proximal to the tissue-penetrating section. The fluid delivery section is configured to deliver fluid in a specific direction, or a selectable direction. In some variations, the fluid delivery section is configured to deliver fluid from the injector in a direction that is different from the direction of tissue penetration.

As previously mentioned, the injector may be manually or automatically extended (and/or retracted). In general, automatically extended injectors may include a trigger that releases the injectors from the body of the catheter. Before it is released, the injector (or injectors) is protected from contacting and possibly damaging the vessel wall as the catheter is positioned. After triggering the automatic release of the injector, at least the distal most tip of the injector is released from the body and extends from the exit port. For example, the injector may be spring loaded so that it is released upon release of a structure (e.g., a sheath or cover) holding it in the catheter. In some variations at least a portion of the injector is formed of (or connected to) a shape memory material (e.g., a nickel titanium alloy) that changes shape to extend the injector.

Figure 2D:
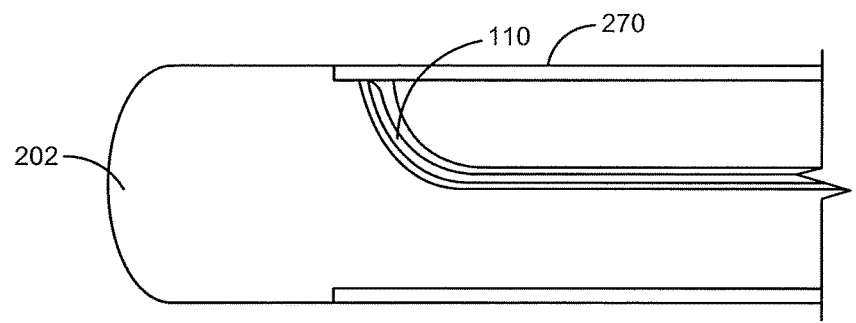
Figure 2E:
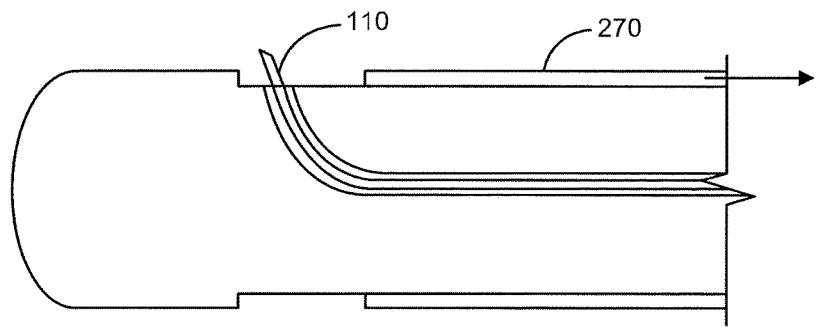

FIGS. 2D-2E shows one variation of an injection catheter 202 having an automatically extending injector 110. As shown in FIG. 2D, the injector 110 can be kept within the body of the catheter and held secured by a cover 270. The cover 270 can be been removed (e.g., by sliding to the right), as shown in FIG. 2E, which can allow the injector 110 extend from the catheter. In some variations, the injector 110 may also be automatically or manually retracted after it is deployed automatically, (e.g., and the cover 270 may be replaced). In some variations, replacing the cover 270 retracts the injector 110. Any appropriate trigger may be used, and any appropriate automatic extension may be used (e.g., springs, pneumatic extension, magnetic extension, etc.). The injector shown in FIGS. 2D-2E extends from the body of the injection catheter 202 in a predetermined angle that is not perpendicular to the injection catheter, as shown. In general, the injector 110 may extend from the injection catheter body in any appropriate direction.

In some variations using catheters having one or more automatically extending injectors, the catheter may be positioned, and the injector (or injectors) may be extended. When multiple injectors are used, the same trigger may extend or allow all of the injectors to be extended simultaneously or individually. Once the injector is extended, it may then be positioned against the vessel to allow penetration. This variation (using multiple injectors for simultaneous penetration) may be particularly useful when delivering fluid to the extraluminal space immediately adjacent to the vessel.

The injector 110 may be controlled to determine the direction and extent to which it extends from the catheter. For example, the injection catheter may include a guide, track, or channel (including a keyed channel, as described previously) to control the direction of movement of the injector. In some variations, the injection catheter comprises a deflection plate within the lumen of the catheter to direct the injector (as it is being extended) from the lumen of the catheter through the exit port in a continuous direction. In some variations, this deflection plate can be adjusted to change the angle at which the injector extends from the catheter body.

Figure 3A:
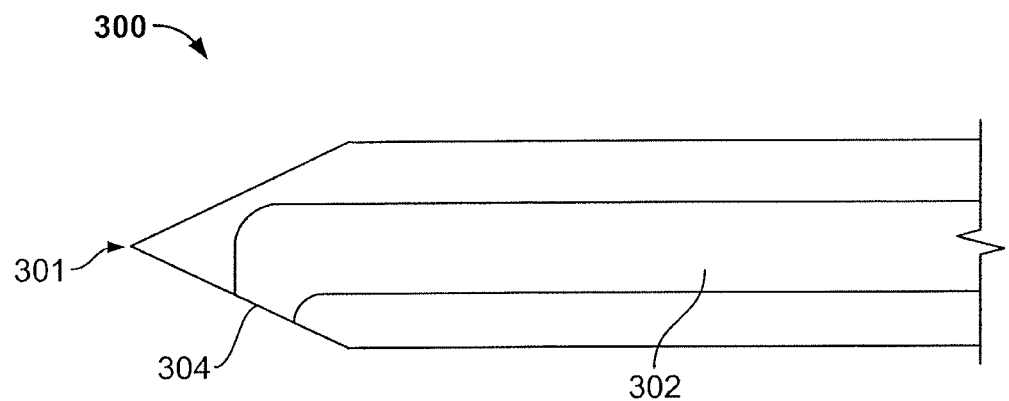
FIGS. 3A-3E show cross-sectional views of different variations of the injectors described herein.

FIGS. 3A-3E show cross-sections of different variations of the tissue-penetrating section and fluid delivery section of directional injectors. For example, FIG. 3A shows the distal end of an injector 300 having a pointed tip 301. The injector contains a passage 302 through which the fluid to be injected can pass. This passage 302 is connected to the opening 304 of the fluid delivery section to allow fluid to be released. As shown in FIG. 3A, the fluid delivery section is located on the angled portion of the tissue-penetrating section, and therefore fluid released from the injector may be released in a direction normal to the angled portion. In this variation, fluid is only released from this one exit of the fluid delivery section.

Figure 3B:
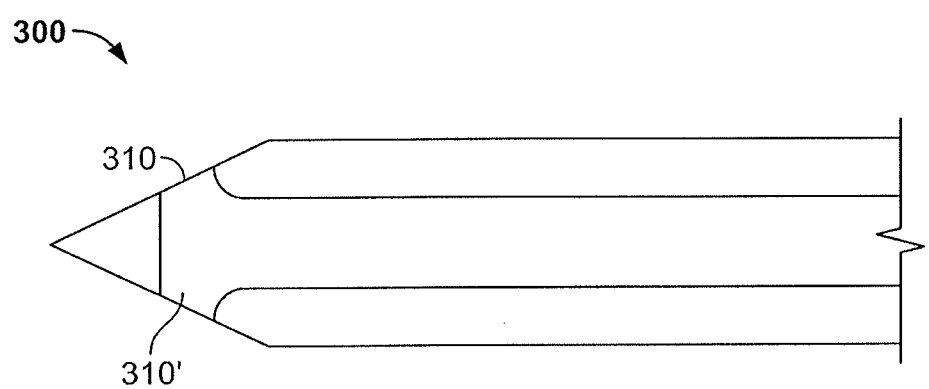
Figure 3C:
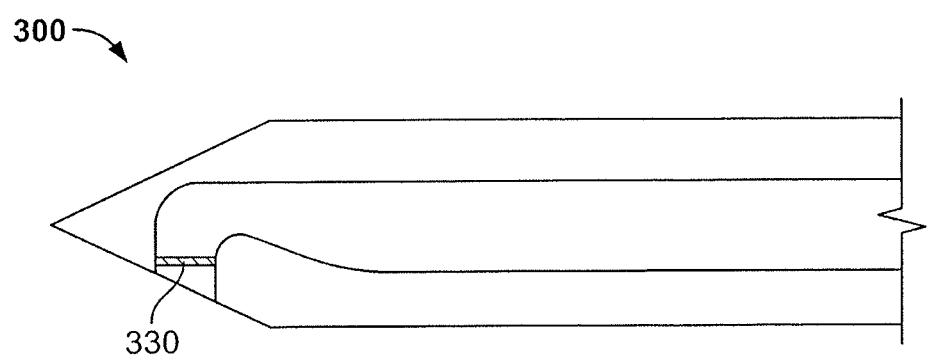
Figure 3D:
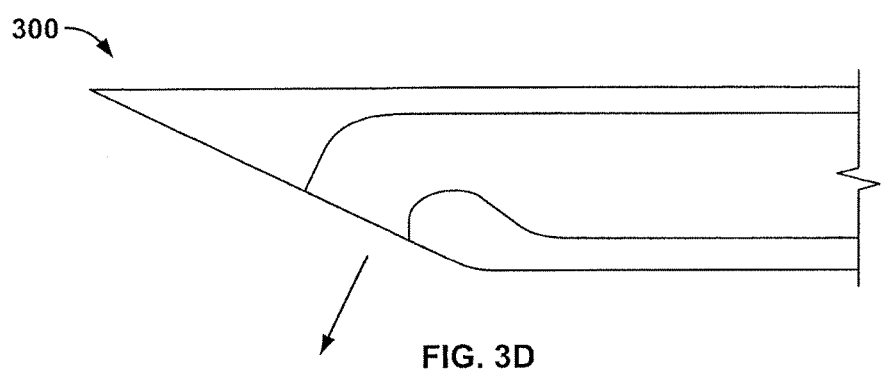

FIG. 3B shows another example of an injector 300 in which fluid is released from the fluid delivery section through two openings 310,310'. The directional injector maximizes the channeling of fluid along anatomical tissue and fascia planes, allowing the majority of the fluid to efficiently reach the target tissue, even when the target tissue is distant from the injector entry site, without having to reposition the injector.

Figure 3E:
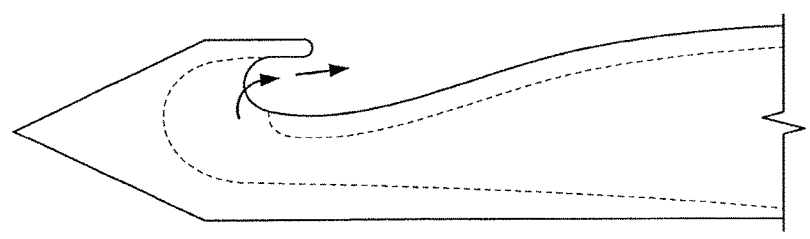

The direction that fluid exits the directional injector 300 may be determined by the configuration of the fluid delivery section. For example, in some variations, the fluid delivery section releases the fluid in a direction that is opposite to the direction of extension of the injector 300 (e.g., in the proximal direction of the injector). FIG. 3E shows one variation of an injector 300 in which fluid exits the injector in the proximal direction (indicated by arrow). Another variation is shown in FIG. 5B.

The flow of fluid from the directional injector may also be regulated, as described above. For example, the directional injector 300 may include buffers, baffles or other structures to prevent fluid leaving the injector from injuring the tissue. For example in FIG. 3C, the fluid delivery section includes a filter 330 through which fluid must pass before it can exit the injector. The internal lumen shape within the injector 300 may also be configured to affect the flow rate and direction of fluid leaving the injector. For example, the lumen may include a widening of the passage to reduce the flow rate as the fluid leaves the injector.

The tissue penetrating region of the injector may be any shape appropriate to penetrate the tissue, including sharp, beveled, pointed, rounded and dull shapes. For example, in FIG. 3D, the injector 300 has a beveled shape. In general, the injector may have an overall needle-shape, allowing it to readily penetrate the tissue. In the examples shown in FIGS. 3A-3D, the fluid delivery section is located on the side of the tissue-penetrating section (and the tissue-penetrating section and the fluid delivery section overlap). In some variations, the injector may be a needle having a very small gauge (e.g., 20-30 gauge needle), and the fluid delivery section is located at the distal end of the injector.

Figure 4A:
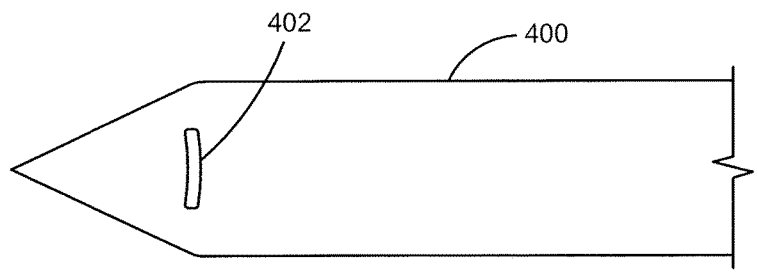
FIGS. 4A-4C show views of different injectors as described herein.
Figure 4B:
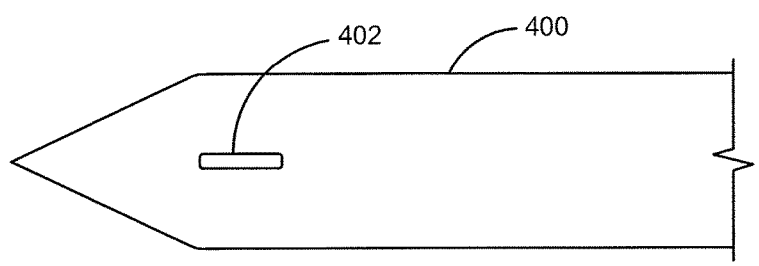
Figure 4C:
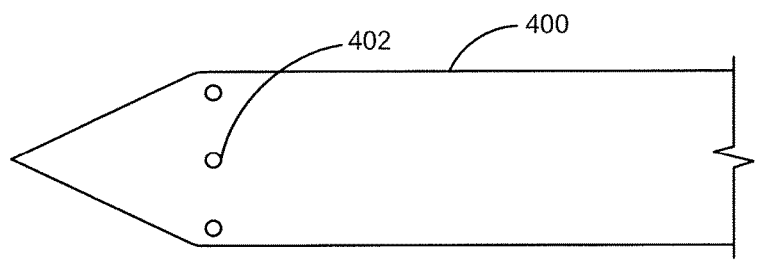

FIGS. 4A-4C show additional views of injectors 400. In these examples, the fluid delivery outlet 402 is located more proximally, such as closer to the tissue-penetrating section. The fluid delivery outlet 402 comprises one or more openings that are shaped to regulate the flow and direction of fluid therefrom. For example, in FIG. 4A, fluid released from the fluid delivery outlet 402 would fan out in a plane that is perpendicular to the injector. Similarly, in FIG. 4B, fluid released from the fluid delivery outlet 402 would be ejected in a plane that is parallel to the injector 400. Thus, it is possible for the shape and orientation of the fluid delivery section to control the way that fluid is released.

In some variations, different injectors may be used with the same injection catheters. For example, the catheter may have an elongate channel that extends proximally to hold an injector that can be withdrawn and inserted (and extended) through the channel. Thus, injectors may be "swapped out" as needed with other injectors, based on the geometry of the target tissue, or the relationship between the vessel and the target tissue. In some variations this may not be possible, because the injector may be fixed within the injection catheter.

Described below are examples of the methods of using the injection catheters described herein.

EXAMPLE 1

Surgical procedures (particularly percutaneous catheter-based procedures) may cause inappropriate nerve stimulation or even nerve damage. Anesthetizing only the nerve, or a sub-region of the nerve may prevent pain, damage to the nerve, or damage to the patient that can result from improper neural activity. For example, the carotid body may be impinged during carotid angioplasty, stent delivery or other procedures performed in the carotid artery. This may cause profound bradycardia or asystole. Clinical evidence suggests that in patients undergoing carotid surgery (endarterectomy), direct application of anesthetic at the bifurcation can render the carotid body quiescent.

One variation of the methods described herein is a method of selectively applying anesthetic to a subject's carotid body from within the carotid artery to prevent such problems. The method involves inserting an injection catheter into the carotid artery, positioning the injection catheter within the carotid artery near the carotid body, anchoring the injection catheter before extending the directional injector of the injection catheter to selectively deliver anesthetic to the carotid body, and applying anesthetic from the injection catheter to the sinus nerve.

Figure 5A:
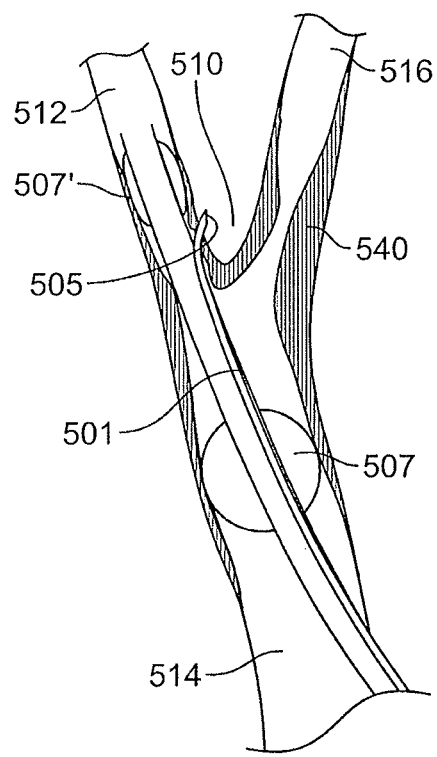
FIGS. 5A-5B show one variation of a method for selectively applying anesthetic to a target tissue.
Figure 5B:
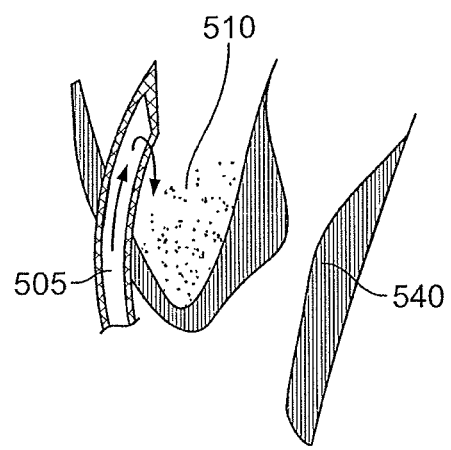

FIGS. 5A and 5B illustrate an example of the method described above. In FIG. 5A, an injection catheter 501 has been positioned so that the exit port for the injector 505 is adjacent to the carotid sinus 510. The injection catheter 501 straddles the external carotid artery 512 and the common carotid artery 514. The injection catheter 501 has been secured in the artery lumen by the two holdfast balloons 507, 507' attached to the injection catheter 501, and the injector 505 has been advanced into the target area, such as the carotid sinus 510. The distal end of an injector may be coated or filled with a radiodense metal or resin to facilitate visualization of the needle tip.

Anesthesia can be applied within the carotid sinus 510, as shown in the magnified view in FIG. 5B. This procedure may be done in conjunction with the TOPS procedure described briefly above, in which the flow of blood through the common carotid artery and the external carotid artery are arrested so that internal carotid artery backpressure sweeps dislodged debris into a lower pressure reservoir, allowing repair of lesions or other procedures. For example, in FIGS. 5A and 5B, the internal carotid artery is shown having a buildup of stiff plaque 540. Removal of this plaque (e.g., by angioplasty, scraping, etc.) may otherwise improperly stimulate or impinge on the sinus nerve. The method described herein may be used to apply anesthetic to reduce unwanted effects.

Providing anesthetic to nerves such as the carotid sinus nerve or the carotid body can be particularly useful before performing intravascular procedures near the nerve. For example, during angioplasty procedures, it may be beneficial to provide anesthetic to nearby nerves (such as the carotid sinus nerve) before beginning the angioplasty procedure, while avoiding involvement with the recurrent laryngeal nerve, phrenic nerve, superior laryngeal nerve, hypoglossal nerve, facial nerve, or vagus nerve. Indiscrete application of anesthetic to these nerves can occur immediately or through diffusion from larger volumes of anesthetic delivered without directional application. This may result in detrimental changes to speech, respiration, swallowing and facial expression, leading to poor subject experience, difficulty communicating, respiratory distress, and aspiration pneumonia.

EXAMPLE 2

The devices and methods described herein may also be used to improve surgical procedures on the vessels themselves. For example, fluid may be used to fill the space in the fascia around the vessel so that it swells or becomes tumescent. This both narrows the vessel (making it easier to ablate or operate on) and may separate the walls of the vessel that are subject to the heat or pressure of the surgery from adjacent structures that may otherwise be injured. Tumescence is generally temporary, as the fluid is absorbed by the tissue over time. This procedure may be referred to as tumescent anesthesia.

In typical tumescent anesthesia, a small needle (e.g., 27 to 30 gauge) is generally used from outside of the body to first numb the skin in multiple locations, and then a larger needle (e.g., 19 to 25 gauge) is used to load the larger volume of tumescent fluid at an acceptable rate again at multiple locations. However, this method is both inaccurate, time consuming, and potentially dangerous, as it risks injuring other regions of tissue than the target region. In particular, when the procedure to be followed involves operating on the walls of a vessel (e.g., by ablating with electrical energy), it would be much better to apply fluid beneath the fascia surrounding the vessel, so as to insulate nearby tissue structures. For example, tumescent anesthesia may be helpful when applying heat, laser, or electrical energy to ablate regions of a blood vessel wall.

In general, blood vessels follow the same histological makeup: the inner lining is the endothelium, followed by subendothelial connective tissue, and then a muscular layer of vascular smooth muscle (media). Finally, there is a further layer of connective tissue (adventitia), which contains nerves that supply the muscular layer, as well as nutrient capillaries in the larger blood vessel. The blood vessel may be within a fascial layer. Thus, the methods described herein may be used to apply fluid (including but not limited to fluid containing anesthesia) to create tumescence between these layers (e.g., between the adventitia and the fascial layer).

In this procedure, fluid is injected into the tissue from within the blood vessel, rather than external to the subject, avoiding the separate punctures of the skin. The injection catheter may comprise any of the catheters described above, and may have an injector with a delivery tube for the anesthetic solution that is in the 21 to 30 gauge range for remote instillation of fluid into the extraluminal space. Furthermore, the region of the vessel made tumescent by the method described herein may be specific to the region that will be treated. In some variations, the injection catheter used to inject the solution causing tumescence may include one or more ablation electrodes for treating the vessel.

Figure 6A:
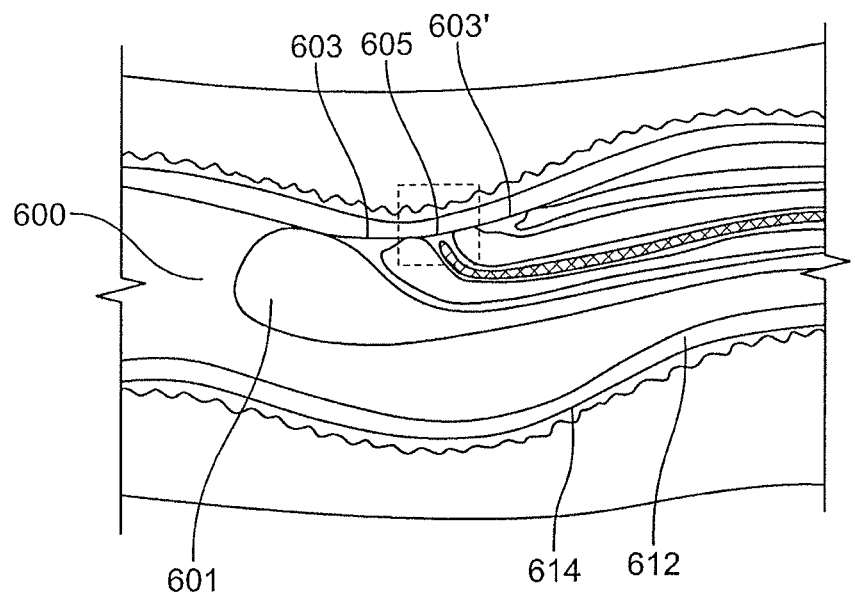
FIGS. 6A, 6B and 6C illustrate one variation of a method for creating tumescence from an injection site within a vessel, as described herein.
Figure 6B:
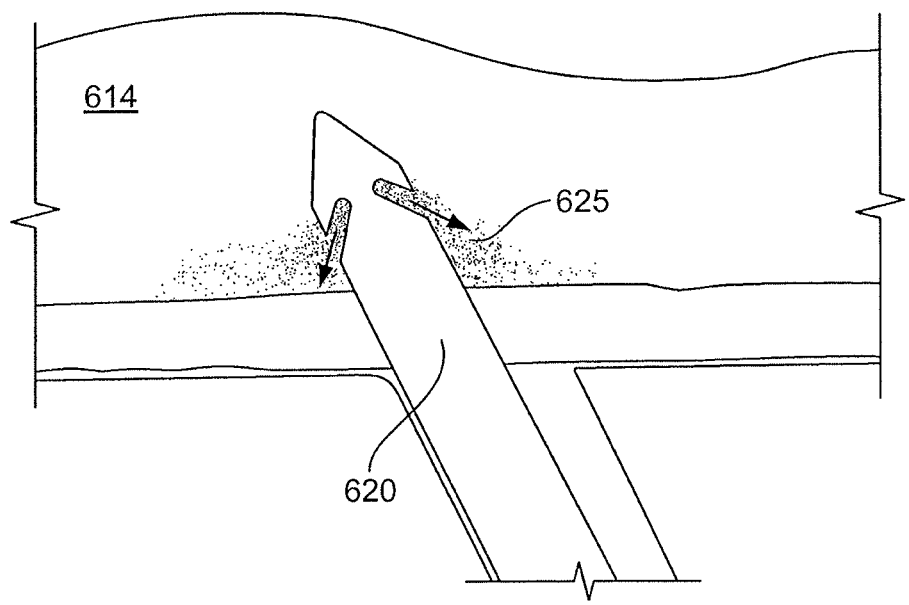
Figure 6C:
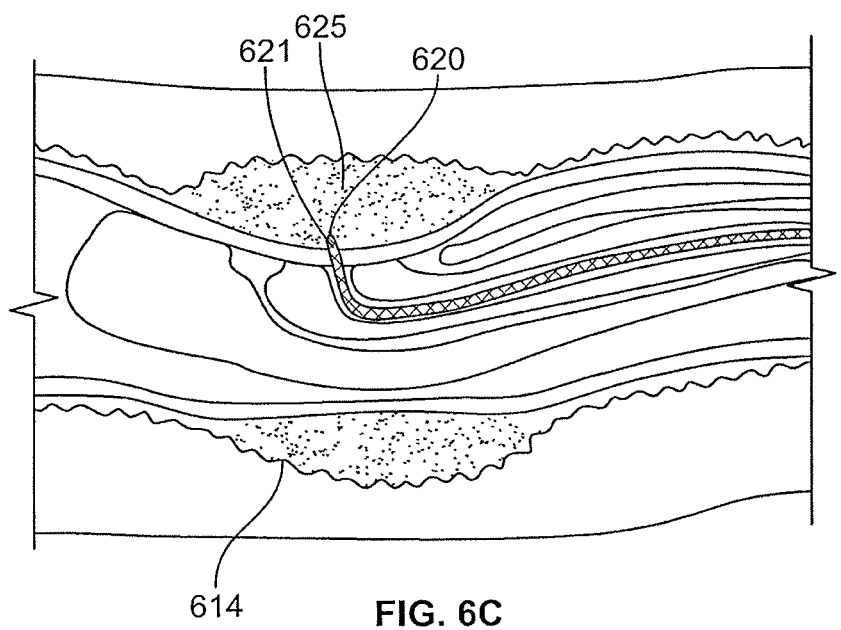

Any appropriate amount of fluid used to create the tumescence may be added, and this may be monitored by ultrasound. Generally, even though fluid enters the extraluminal space from a single insertion (e.g., a single injector), the fluid may spread to surround the vessel, following the planes of the fascia in the space between the adventitia and the fascial layer (e.g., the subfascial layer). FIGS. 6A-C illustrates an example of this method.

In FIG. 6A an injection catheter 601 has been positioned within a vein 600, as described, and the holdfast (here consisting of two suction-type holdfasts 603, 603' surrounding the injector exit port 605) has secured the injection catheter against the wall of the vein 600. The endothelium 612 and subfascial layer 614 are also indicated. FIG. 6B shows a magnified view of the injector from FIG. 6A after it has been extended into the subfascial layer 614 (also shown in FIG. 6C), and has begun applying fluid 625 (schematically illustrated as the speckled pattern). The fluid is released by the injector in a substantially proximal direction with respect to the injector (as indicated by the arrows). Thus, the fluid 625 is released into the layer 614, and the force of release of the fluid does not damage the tissue or impinge on neighboring layers. In addition, the layer will serve as a channel or guide for the fluid.

FIG. 6C shows the injector 620 after it has injected a substantial amount of fluid 625 into the subfascial layer 614, creating tumescence which has both reduced the diameter of the vessel 600, and has increased the distance between the outer wall of the vessel 612 and any nearby structures. Once adequate tumescence has been established (as viewed by ultrasound, for example), the injector can be withdrawn and the catheter advanced to a nearby region if further tumescence of this vessel is desired. The vessel can then be treated, e.g., by ablation or application of energy.

In this example, the structure is anesthetized by the addition of a solution containing anesthesia to create tumescence and it is localized with ultrasound guidance. As described above, the solution need not contain anesthesia. Furthermore, although this example shows a vacuum-type holdfast, any appropriate holdfast (or injector) may be used as part of the injection catheter.

Without the methods described herein, the use of tumescent anesthesia is both difficult and potentially dangerous. For example, in thin patients, the tumescent fluid must be applied just under the skin where it is hard to see the needle. In deep structures, the needle may not be easily visualized or multiple adjustments may be needed to the ultrasound probe orientation to align it with the needle and the structure to be treated. For example, the treatment of the short saphenous vein in the posterior calf currently requires the patient to be supine or in an awkward bent position to allow sufficient space to place the ultrasound probe and to allow the operator to see the alignment of the needle to the ultrasound probe. Treatment in the supine position requires repositioning, repreparing and red raping of the patient to subsequently treat veins on the anterior surface of the body.

The use of the methods and apparatuses described herein can also be applied to procedures such as ultrasound, radiofrequency or laser ablation of venous structures for varicose veins or chronic venous stasis. Both techniques have an incidence of parasthesias from injured nerves that run adjacent to the vein. Heat energy that is not effectively buffered by tumescent fluid may result in damage to subcutaneous and skin tissues. In particular, the increased incidence of post procedure bruising and pain from treatment with the hotter laser catheter may be avoided using endolumenal tumescent injection that more accurately deploys a greater volume of tumescent fluid adjacent to the vein and avoids skipping areas resulting in poor tumescence.

In addition, the use of the methods and apparatuses described herein can also be applied to procedures that apply either fluids or energy to target locations within the body, particularly in order to alter the functioning of one or more nerves. Various methods and embodiments of catheters including injectors and energy applying features for delivering various forms of fluid and energy (e.g., RF and ultrasound) for altering the functioning of nerves are described below. In addition, any of the features, functions or methods described above can be included with, or in replace of, one or more features, functions or methods described below for catheters which can either apply fluids or energy to target locations for altering the functioning of nerves.

Furthermore, the space from skin to the vessel created by the tumescent fluid layer decreases with time as fluid diffuses into the surrounding tissues. The direct application of fluid to the perivascular space alone and the ability to easily instill fluid at the time of active ablation allow maximal separation of the heat source from nerve, skin and subcutaneous tissue. The fluid can also be cooled down (e.g., to near freezing) to further reduce damage to surrounding tissues. The method of endolumenal delivery of tumescent anesthesia can allow direct placement of fluid adjacent to the active heating element used for ablation, and this fluid can absorb some of the heat energy before it has a chance to harm adjacent structures. This could be particularly useful for treating the short saphenous vein where the nerve courses more closely with the vessel. Currently, the most prudent approach used is to treat a short segment of the proximal vein where the nerve is generally more separated from the vein. This method is less desirable than the method outlined herein, because treatment of a short segment increases the risk of failed closure of the vein or reflux of blood from branches below the treated vein. The techniques described above may enable safe treatment of a longer length of vein, thereby improving results.

Figure 7A:
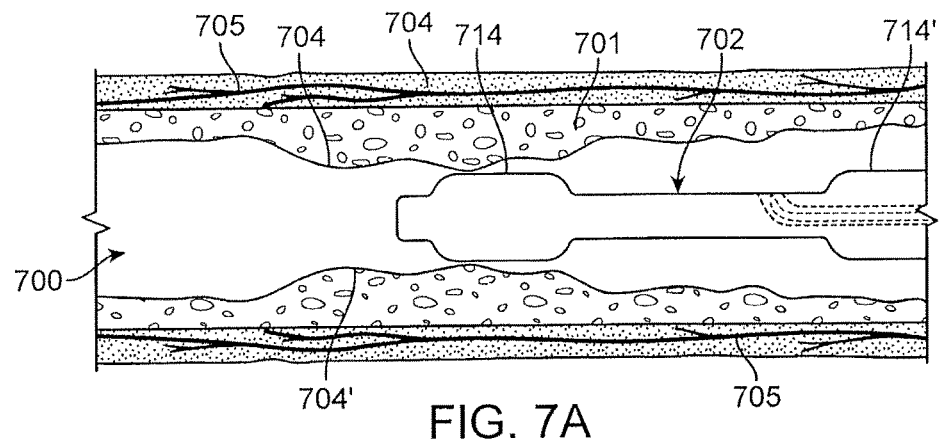
FIGS. 7A-7D illustrate methods and devices for delivering fluid for denervating a nerve, such as at least a part of the renal SNS.

FIGS. 7A-7E illustrate another variation of devices and methods for applying fluid in a target area or location in order to alter the function of nerves, including denervation of nerves for treating hypertension. In FIG. 7A, a catheter 702 is located within the lumen 700 of a vessel. The walls 701 of the vessel can be irregular 704, 704' (e.g., as might be found in an artery or other vessel). Adjacent to a portion of the vessel wall 701 is the adventitia 704 with at least one nerve 705 extending through the adventitia 704. The catheter 700 can include at least one injector 710 which can exit the catheter 702 from an exit port 712 (see FIG. 7D). The catheter 702 can also include at least one holdfast, such as inflatable balloons 714 and 714' on either side of the exit port 712 for assisting in positioning the injector 710.

Any number of holdfasts can be included with the catheter 702 and positioned in any number of ways relative to the injector 710. In addition, one or more of a variety of holdfasts, including the holdfasts discussed above, for example, the holdfasts shown in FIGS. 2A-2C, can be included with the catheter 702. Additionally, any of the holdfasts discussed herein can be included with at least any of the catheters disclosed herein without departing from the scope of this disclosure. For example, catheter 702 can include one or more vacuum-type holdfasts (see FIG. 2C) which can allow the catheter 702 to be suctioned against the vessel wall 701 prior to and during injection of fluid into the adventitia 704, such as for denervating renal nerves, or at least a part of the renal SNS, for treating hypertension.

Figure 7B:
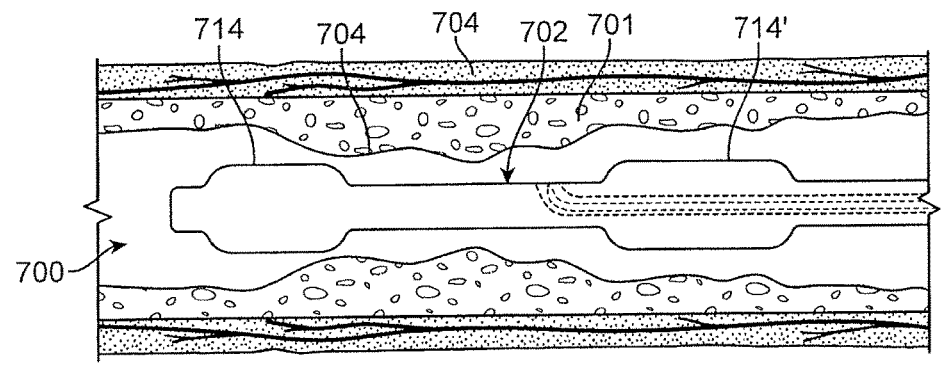
Figure 7C:
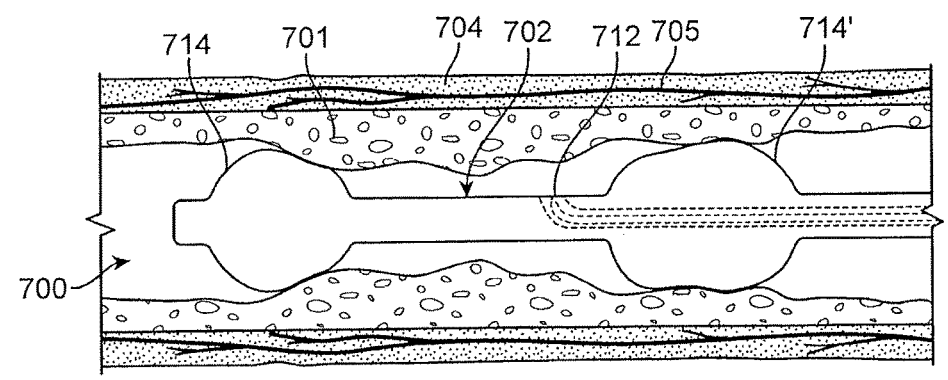

In the transition between FIG. 7A and FIG. 7B, the catheter 702 can be positioned so that the exit port 712 for the injector 710 is positioned near the target location. The target location can be an area adjacent to the nerves 705 extending along the adventitia 704, such as the renal nerves, which extend along the adventitia 704 surrounding the renal arteries. Thus, as shown in FIG. 7B, the catheter 702 can be positioned with respect to the target location. The holdfasts (balloons 714, 714') can then be deployed, in this example by inflating them to secure the position of the catheter 702 within the vessel, as shown in FIG. 7C. The holdfast balloons 714, 714' can provide support against the uneven walls of the vessel 704, 704' and prevent the catheter 702 from moving. The balloon-type holdfasts can expand radially around the catheter 702 and can serve to center at least a portion of the catheter 702 within the vessel lumen 700.

The balloons 714, 714' (or other holdfasts) may also be asymmetrically positioned, so that the holdfasts can preferentially secure the catheter 702 to one side of the vessel (e.g., maintaining the shortest distance between the injector and the target tissue). Although two holdfasts are shown, it should be clear that no holdfast may be used, or that only one holdfast may be used, although in some variations more than one holdfast may be used (as shown). Furthermore, the position of the holdfast with respect to the exit port 712 for the injector 710 may also vary. In some variations, the holdfast may surround the exit port 712 (and may include a passage for the injector). In some variations the holdfast (or holdfasts) can be located proximally or distally to the exit port 721 for the injector 710.

Figure 7D:
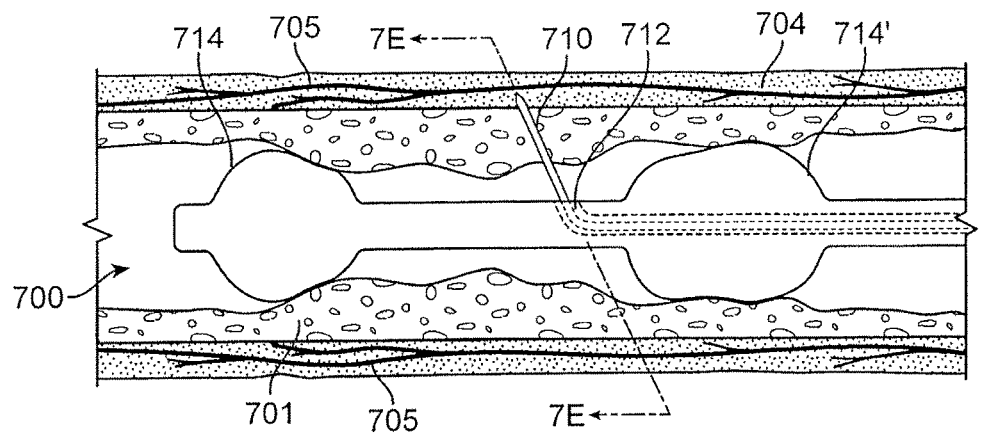

Once the catheter 702 has been secured into position so that the exit port 712 for the injector 710 is located within reach of the target location when the injector 710 is extended, the injector 710 may be extended through the vessel toward the target location, as shown in FIG. 7D. The injector 710 can be extended from the catheter 702 (through the exit port 712) until the injector 710 penetrates the vessel and approaches the target location, such as the adventitia 704 surrounding the renal artery.

Figure 7E:
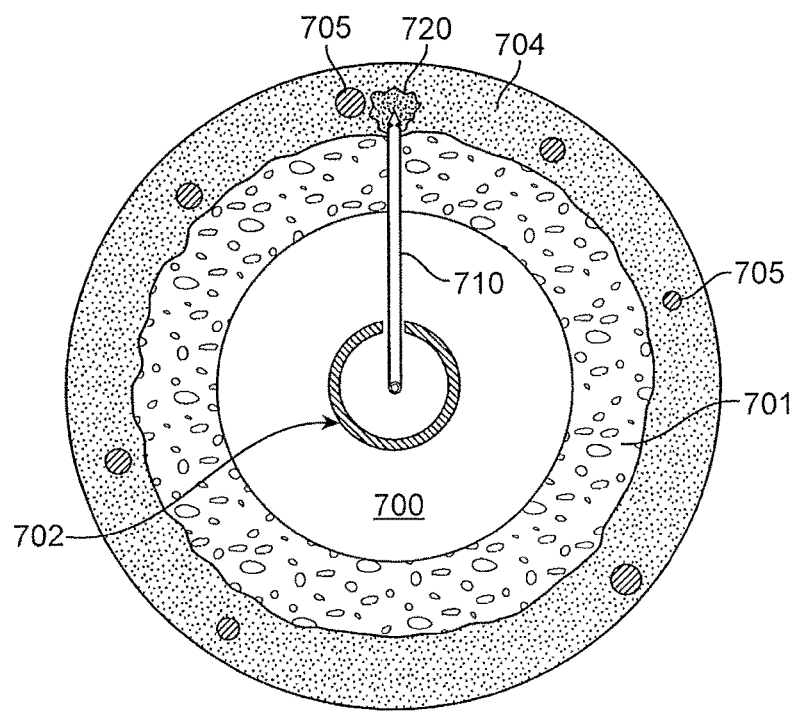
FIG. 7E shows a cross-section view of FIG. 7D taken across cross-section line 7E-7E, which illustrates the delivery of fluid, such as a drug, in the adventitia surrounding the renal artery.

FIG. 7E, illustrates the delivery of fluid 720 (e.g., nerve-blocking drugs, guanethidine) to at least a part of the target location. The fluid 720 can be delivered at or near a target tissue (e.g., nerve, adventitia) in order to achieve a desired result. For example, the fluid 720 can be delivered into the adventitia 704 surrounding the renal artery in order to allow the fluid 720 to travel to nearby nerves 705, such as the renal nerves, and affect their functioning (e.g., denervate the nerves 705). Any of the tissue-penetrating and fluid delivery sections of directional injectors described above, such as in relation to FIGS. 2D-4C, can be implemented in the catheter 702 for providing fluid in order to affect the functioning of a nerve without departing from the scope of the present disclosure. Once the fluid delivery section of the injector 710 is properly positioned, such as within the adventitia 704, an appropriate amount of fluid 720 (e.g., nerve-blockers) can be injected within at least a part of the target location.

Alternatively or in addition, the target location can include any number of tissues within the body, including tissues comprising or surrounding the renal vein, renal artery, carotid artery, or carotid body. For example, the catheter 702 can be positioned such that the injector 710 can be extended from the catheter (through the exit port 712) until the injector 710 penetrates at least a part of the carotid body. One or more fluids 720 (e.g., nerve-blockers, guanethidine, etc.) can be delivered to at least a part of the carotid body in order to alter the functioning of nerves within the carotid body. As discussed above, the carotid body can assist in a variety of physiological conditions, including blood pressure. Therefore, altering the nerve functioning of at least a part of the carotid body can result in physiological changes, such as treating hypertension.

In addition, various forms of energy can be applied to one or more target locations. Similar to what has been discussed above, various forms of energy can be applied to one or more target locations in order to alter the functioning of one or more nerves, such as the renal nerves or carotid body. With the application of energy, such as RF energy or ultrasound energy, tissue can be altered such that one or more nerves at least reduce their ability to transmit signals, including denervation of the nerves. Catheter embodiments described below include catheter configurations for delivering RF energy and ultrasound energy. However, catheters can be configured to apply any number of forms of energy.

In addition, catheters configured to provide energy, such as RF and ultrasound energy, can also be configured to apply one or more fluids, such as at or near the target location. Additionally, fluids can be applied at or near the target location at least one of before, during or after applying energy to the target location. Furthermore, the energy providing features (e.g., electrodes, transducers, acoustic elements, etc.) can be positioned on an extending element, such as the injector 710 described above, in order to allow direct contact of any of the energy providing features with the target tissue or target location. In addition, energy providing features can be positioned in any number of a variety of configurations relative to each other and the target location in order to affect the energy delivery area and extent of tissue alteration or damage. Some device and method embodiments of catheters configured to provide energy to target locations are described, for example, below.

Figure 8:
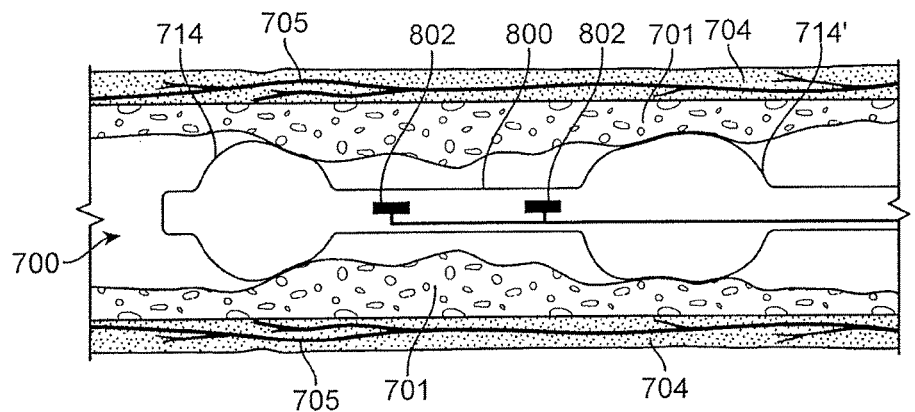
FIG. 8 illustrates an embodiment of the catheter including a pair of electrodes for providing RF energy to a target location within the body.

FIG. 8 illustrates an embodiment of a catheter 800 which can provide RF energy to at least one target location. The catheter 800 can include at least one electrode 802 which can be electrically coupled to a powering and control unit (not shown). Once the electrodes 802 are positioned relative to the target location, the powering and control until can control one or more of a variety of factors (e.g., energy intensity, duration of energy application, etc.) associated with applying RF energy to the target location. The factors can vary depending on, for example, at least the size of the target location and the desired extent in tissue damage or desired tissue alteration within the target location.

At least one target location can include the adventitia 704 surrounding the renal artery or the carotid body, such as for treating hypertension by denervating or altering the nerve functioning of the renal nerves or carotid body. FIG. 8 illustrates the catheter 800 positioned in a body vessel 700, such as the renal artery. Any number of holdfasts, including one or more balloons 714 and 714' as shown in FIG. 8, can be included with the catheter 800 in order to position and stabilize the catheter near the target location. For example, the holdfasts can secure the positioning of the electrodes 802 such that when RF energy is released from the electrodes 802, the RF energy is applied to the target location, such as the adventitia 704 and renal nerves 705 surrounding the renal artery. In addition, any number of holdfasts can be included with the catheter 800 and positioned in any number of ways relative to the electrodes 802. In addition, one or more of a variety of holdfasts, including the holdfasts discussed above, for example, the holdfasts shown in FIGS. 2A-2C, can be included with the catheter 702.

Figure 11:
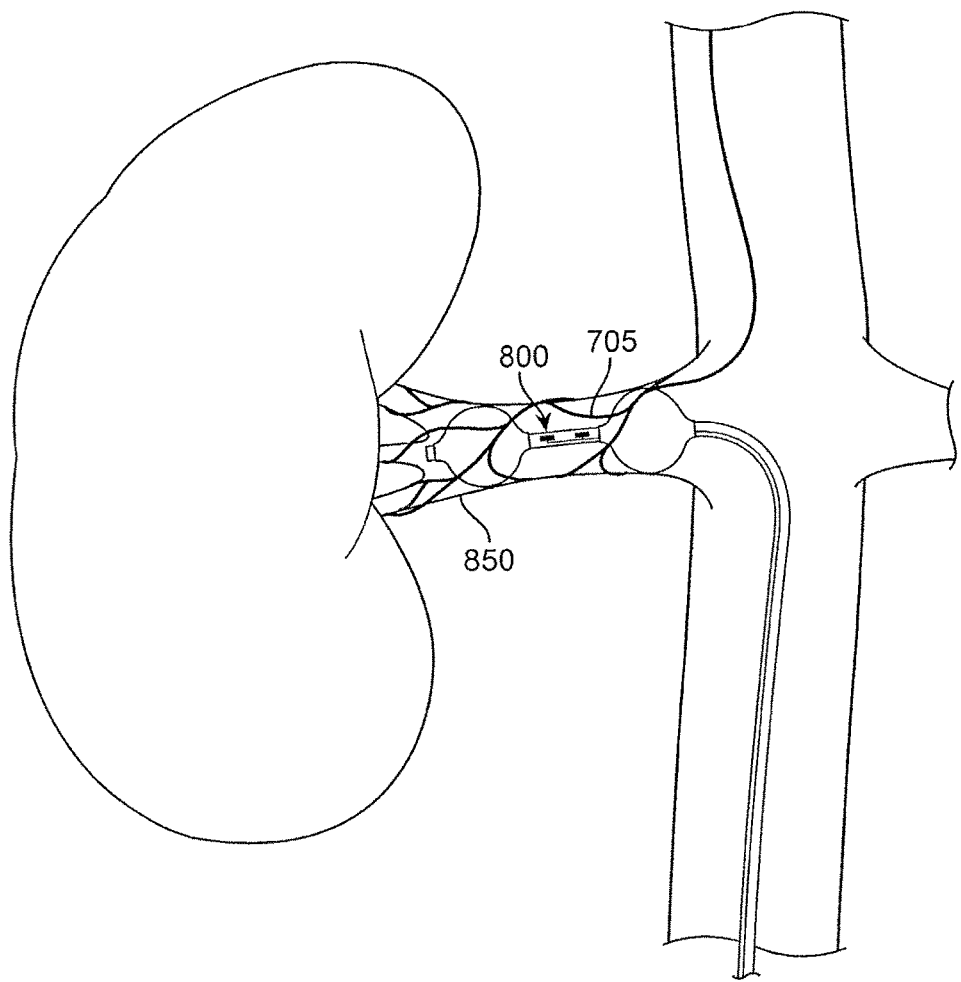
FIG. 11 illustrates the catheter of FIG. 8 positioned in the renal artery with the renal SNS extending along the renal artery.

FIG. 11 illustrates the catheter 800 positioned in the renal artery 850 with the renal nerves 705 extending along the renal artery. The holdfasts can secure the catheter 800 in the renal artery prior to and during the application of RF energy to the target location, which can include the adventitia and renal nerves 705. As discussed above, altering the functioning of the renal nerves, including denervation, can assist in treating hypertension. Therefore, the electrodes 802 of the catheter 800 can be positioned such that they can deliver RF energy to at least one renal nerve renal SNS705 in order to denervate the at least one renal nerve renal SNS705 for treating hypertension in the body.

Figure 9:
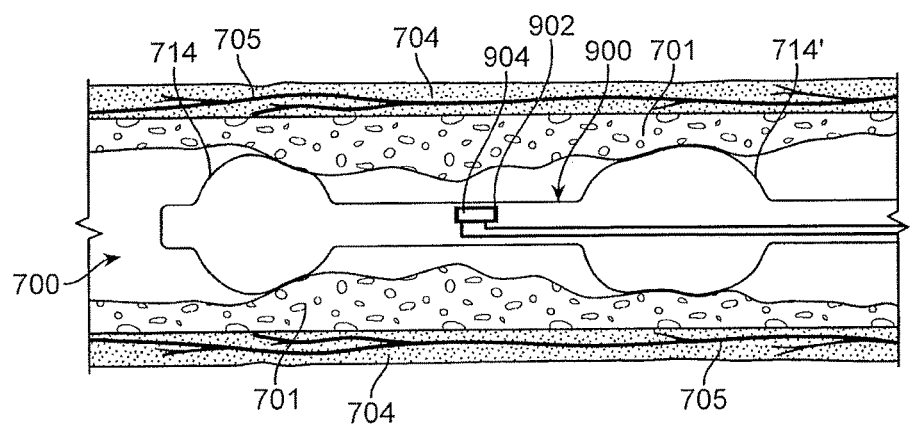
FIG. 9 illustrates an embodiment of the catheter including a transducer with an acoustic element for providing ultrasonic energy to a target location within the body.

FIG. 9 illustrates an embodiment of a catheter 900 which can provide ultrasound energy to at least one target location. The catheter 900 can include at least one transducer 902 with an acoustic element 904 which can be electrically coupled to a powering and control unit (not shown). Once the transducer 902 with an acoustic element 904 are positioned relative to the target location, the powering and control until can control one or more of a variety of factors (e.g., energy intensity, duration of energy application, etc.) associated with applying ultrasound energy to the target location. The factors can vary depending on, for example, at least the size of the target location and the desired extent in tissue damage or desired tissue alteration within the target location.

Similar to as described above, at least one target location can include the adventitia 704 surrounding the renal artery or the carotid body, such as for treating hypertension by denervating or altering the nerve functioning of the renal nerves or carotid body. FIG. 9 illustrates the catheter positioned in a body vessel 700, such as the renal artery. Any number of holdfasts, including one or more balloons 714 and 714' as shown in FIG. 9, can be included with the catheter 900 in order to position and stabilize the catheter 900 near the target location. For example, the holdfasts can secure the positioning of the transducer 902 and acoustic element 904 such that when ultrasound energy is released from the transducer 902 and acoustic element 904, the ultrasound energy is applied to the target location, such as the adventitia 704 and renal nerves 705 surrounding the renal artery. In addition, any number of holdfasts can be included with the catheter 900 and positioned in any number of ways relative to the transducer 902 and acoustic element 904. In addition, one or more of a variety of holdfasts, including the holdfasts discussed above, for example, the holdfasts shown in FIGS. 2A-2C, can be included with the catheter 900.

Figure 10:
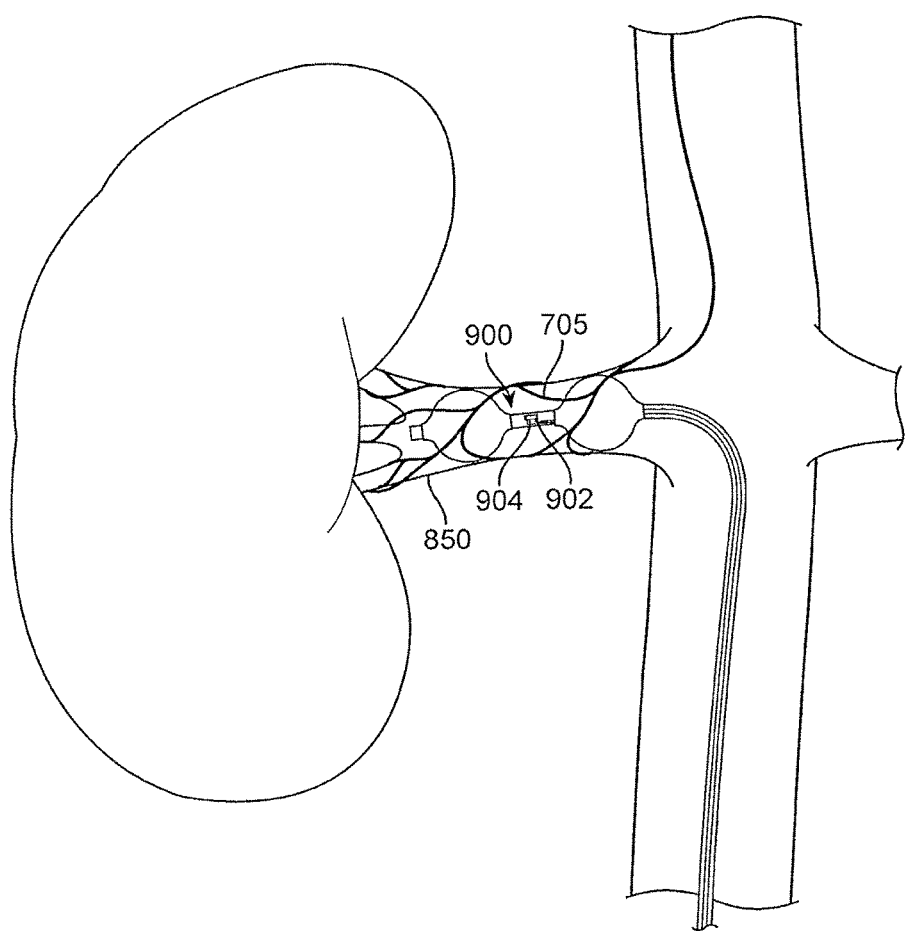
FIG. 10 illustrates the catheter of FIG. 9 positioned in the renal artery with the renal SNS extending along the renal artery.

FIG. 10 illustrates the catheter 900 positioned in the renal artery 850 with the renal nerves 705 extending along the renal artery 850. The holdfasts can secure the catheter 900 in the renal artery 850 prior to and during the application of ultrasound energy to the target location, which can include the adventitia and renal renal nerves 705. As discussed above, altering the functioning of the renal nerves, including denervation, can assist in treating hypertension. Therefore, the transducer 902 and acoustic element 904 of the catheter 900 can be positioned such that they can deliver ultrasound energy to at least one renal nerve renal SNS705 in order to denervate the at least one renal nerve for treating hypertension in the body.

Figure 12:
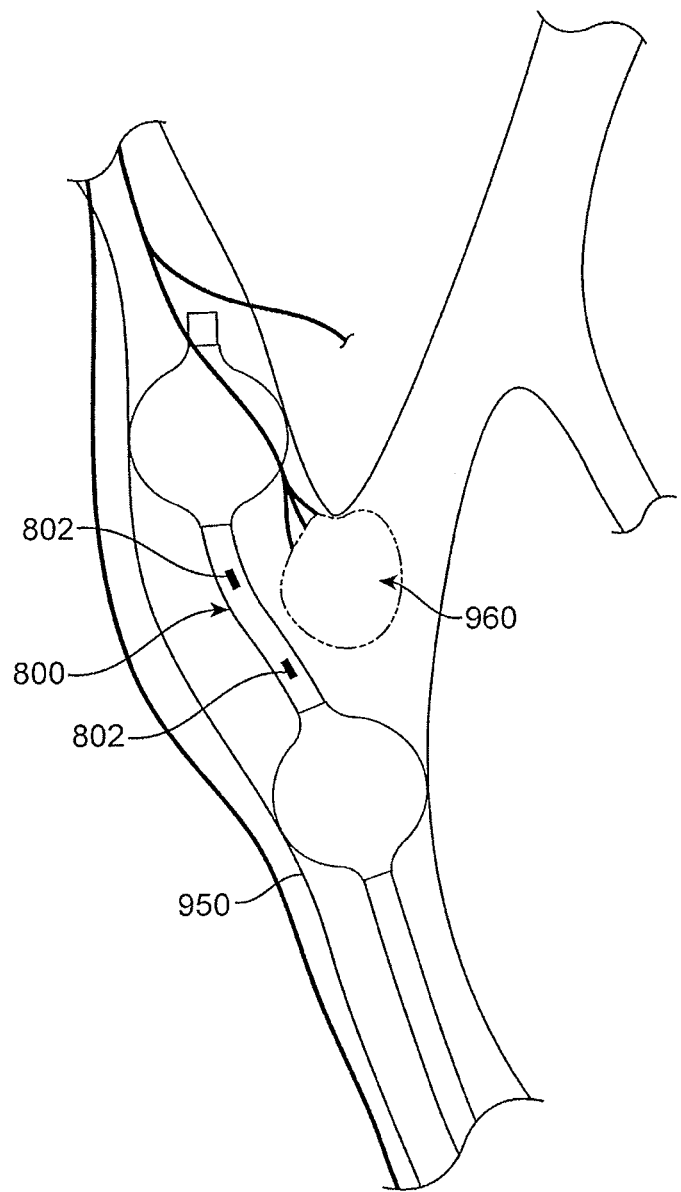
FIG. 12 illustrates the catheter of FIG. 8 positioned in the carotid artery bifurcation showing the electrodes positioned near the carotid body.

The catheters 800 and 900 can also be used to apply energy to various other target locations within the body. For example, FIG. 12 shows the catheter 800 positioned in the carotid artery 950 in order to apply RF energy to a target location at or near the carotid artery, such as the carotid body 960. In addition, the catheter 800 can be secured in position within the carotid artery 950 by at least one holdfast, such as any of the holdfasts included herein, including the inflatable balloons or vacuume-type holdfasts. In addition, the electrodes 802 can be positioned such that they emit RF energy to at least a part of the target location (e.g., carotid body 960). As discussed above, altering nerve functioning of the carotid body 960 can result in improved physiological conditions, such as treating hypertension.

Figure 13:
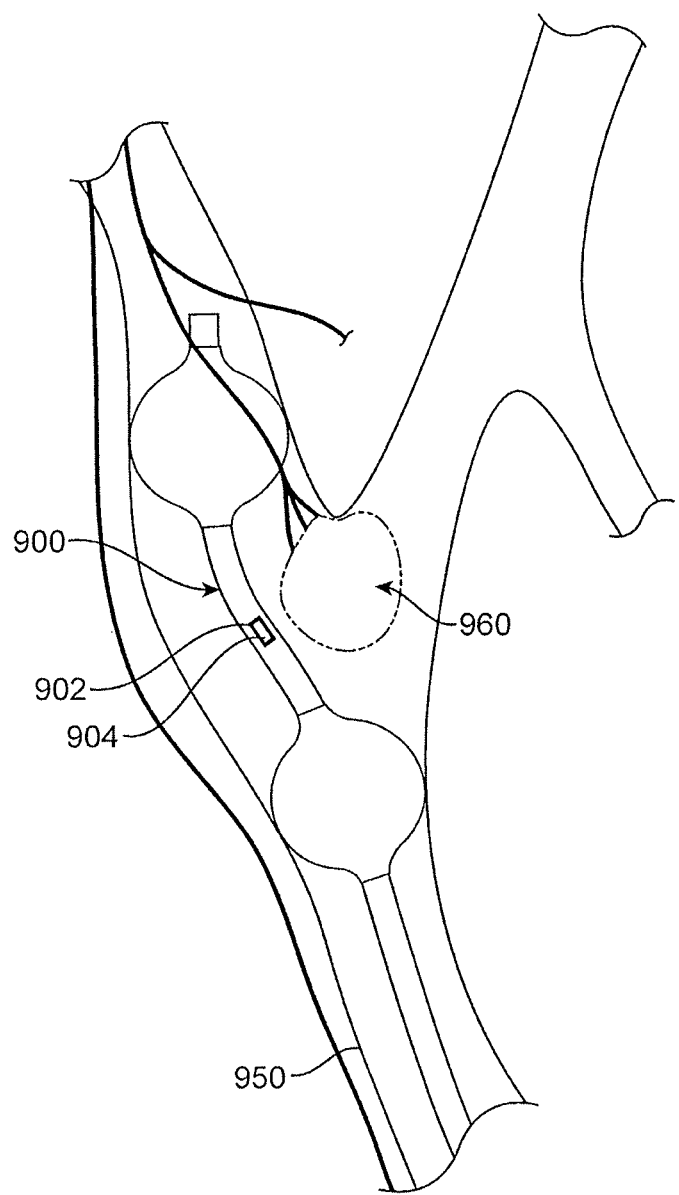
FIG. 13 illustrates the catheter of FIG. 9 positioned in the carotid artery showing the transducer and acoustic element positioned near the carotid body.

FIG. 13 shows the catheter 900 positioned in the carotid artery in order to apply ultrasound energy to a target location at or near the carotid artery 950, such as the carotid body 960. In addition, the catheter 900 can be secured in position within the carotid artery 950 by at least one holdfast, such as any of the holdfasts included herein, including the inflatable balloons or vacuume-type holdfasts. In addition, the transducer 902 and acoustic element 904 can be positioned such that they emit ultrasound energy to at least a part of the target location (e.g., carotid body 960).

Figure 14:
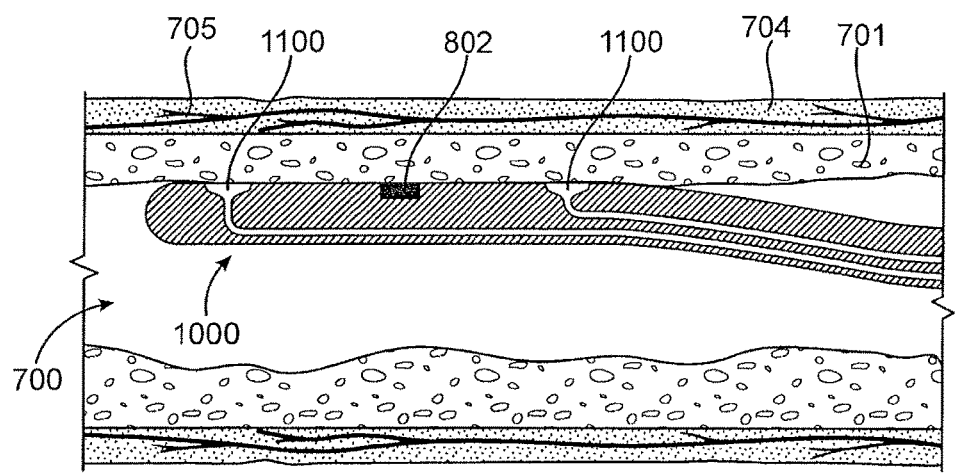
FIG. 14 illustrates another catheter embodiment including vacuum ports for securing the positioning of the catheter and electrodes for delivering RF energy.

For example, a vacuum-type holdfast can be used with at least either of the catheters 800, 900 for securing the catheter 800, 900 against the carotid artery 950 wall at least while applying energy, such either RF or ultrasound energy, to the target location. FIG. 14 illustrates an example embodiments of a catheter 1000 having at least one vacuum port 1100 connected to a vacuum source, such as via a vacuum channel, which can assist in suctioning a part of the catheter 1000 to a part of the vessel wall 701, such as the wall of the renal artery. A vacuum may be applied through these ports 1100 so that when the catheter is brought near the vessel wall 701, the catheter 1000 can suction onto the vessel wall 701 and be securely held. The amount of vacuum may be controlled to prevent damage to the walls 701 of the vessel. Additional variations of the holdfast may also be used (including the balloon-type holdfasts shown in FIG. 8). As previously mentioned, the catheter can include one or more of a variety of holdfasts which can be positioned in any appropriate way, including relative to the energy providing features (e.g., radio-frequency electrodes, transducer, acoustic element).

The vacuum ports 1100 of the vacuum-type holdfasts can allow at least a part of the catheter 1000 to be secured against the vessel wall, such as in order to properly position the energy providing features relative to the target location. As shown in FIG. 14, the vacuum ports 1100 can secure the catheter 1000 in place such that one or more electrodes 802 are positioned relative to the target location such that RF energy can be delivered to at least a part of the target location. For example, the vacuum ports 1100 can suction the catheter 1000 against the wall 701 of the renal artery so that the electrodes 802 can apply RF energy to at least one renal nerve renal SNS705 in order to alter the nerve functioning of the at least one renal nerve renal SNS705.

Figure 15:
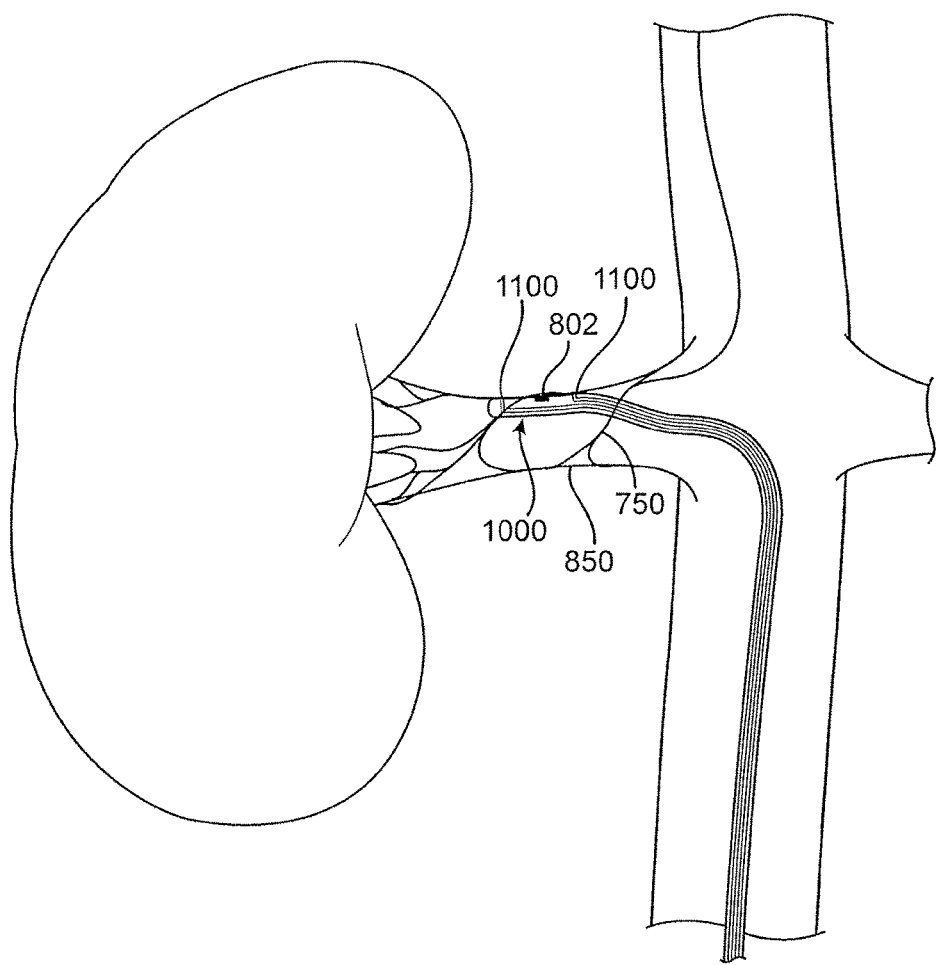
FIG. 15 illustrates the catheter of FIG. 14 positioned in the renal artery with the renal SNS extending along the renal artery.

FIG. 15 illustrates the catheter 1000 positioned in the renal artery 850 with the renal nerves 705 extending along the renal artery 850. The vacuum ports 1100 if the vacuum-type holdfasts can secure the catheter 1000 against a part of the wall of the renal artery 850 at least prior to and during the application of RF energy to the target location, which can include the adventitia and renal nerves 705. As discussed above, altering the functioning of the renal nerves, including denervation, can assist in treating hypertension. Therefore, one or more of the electrodes 802 of the catheter 1000 can be positioned such that they can deliver RF energy to at least one renal nerve 705 in order to denervate the at least one renal nerve for treating hypertension in the body.

While the invention has been described in terms of particular variations and illustrative figures, those of skill in the art will recognize that the invention is not limited to the variations or figures described. In addition, where methods and steps described above indicate certain events occurring in certain order, those of skill in the art will recognize that the ordering of certain steps may be modified and that such modifications are in accordance with the variations of the invention. Additionally, certain steps may be performed concurrently in a parallel when possible, as well as performed sequentially as described above. Therefore, to the extent there are variations of the invention which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed:

1. A catheter device, comprising:
   an elongate body having a distal end and a proximal end;
   a first inflatable holdfast positioned along the elongate body adjacent the distal end of the elongate body;
   a second inflatable holdfast positioned along the elongate body adjacent the first inflatable holdfast, the first inflatable holdfast and the second inflatable holdfast being configured to inflate and anchor the catheter device within a carotid artery; and
   an energy providing feature secured to the elongate body at a first location between the first and second inflatable holdfasts, the energy providing feature configured to deliver energy from the first location,
   wherein the second inflatable holdfast is positioned a distance from the first inflatable holdfast, the distance allowing the energy providing feature to be securely positioned adjacent a carotid body when the first inflatable holdfast and the second inflatable holdfast are inflated within a carotid artery thereby allowing the energy providing feature to deliver energy from the first location to a carotid body.

2. The catheter device of claim 1, wherein the energy delivered to the target area is radiofrequency energy.

3. The catheter device of claim 1, wherein the energy delivered to the target area is ultrasound energy.

4. The catheter device of claim 1, wherein the energy providing feature includes an electrode.

5. The catheter device of claim 1, wherein the energy providing feature includes a transducer and an acoustic element.

6. The catheter device of claim 1, wherein the elongate body has a length suitable for treatment of a carotid body via a transcervical approach.

7. The catheter device of claim 6, wherein the length of the elongate body is within a range of approximately 40 centimeters to 80 centimeters.

8. The catheter device of claim 1, further comprising:
   a passageway extending along a part of the elongate body, the passageway including a distal end positioned at a second location between the first inflatable holdfast and the second inflatable holdfast and
   an injector slidably engaged with the passageway and configured to extend from the elongate body at the second location and into tissue.

9. A method, comprising:
   inserting at least a part of a catheter device into a vessel body, wherein the catheter device includes an elongate body having a distal end and a proximal end, a first inflatable holdfast positioned along the elongate body adjacent the distal end of the elongate body, a second inflatable holdfast positioned along the elongate body adjacent the first inflatable holdfast, wherein the first inflatable holdfast and the second inflatable holdfast are configured to inflate and anchor the catheter device within a carotid artery, and an energy providing feature secured to the elongate body at a first location between the first inflatable holdfast and the second inflatable holdfast, the energy providing feature configured to deliver energy from the first location, wherein the second inflatable holdfast is positioned a distance from the first inflatable holdfast, the distance allowing the energy providing feature to be securely positioned adjacent a carotid body when the first inflatable holdfast and the second inflatable holdfast are inflated within a carotid artery thereby allowing the energy providing feature to deliver energy from the first location to a carotid body;

positioning the energy providing feature of the catheter device within a carotid artery and adjacent a carotid body;

inflating the first inflatable holdfast and the second inflatable holdfast thereby anchoring the catheter device within the carotid artery; and delivering energy from the energy feature to the carotid body.

10. The method of claim 9, wherein the energy delivered to the target area is at least one of radiofrequency energy and ultrasound energy.

11. The method of claim 9, wherein the energy providing feature includes at least one of an electrode, a transducer and an acoustic element.

12. The method of claim 9, wherein the catheter device further includes an extendable injector configured to extend from the elongate body and into the target area for delivering a fluid that causes denervation of at least one nerve.

13. The method of claim 9, wherein the elongate body has a length suitable for treatment of a carotid body via a transcervical approach.

14. The method of claim 13, wherein the length of the elongate body is within a range of approximately 40 centimeters to 80 centimeters.

15. The catheter device of claim 8, wherein the first inflatable holdfast and the second inflatable holdfast are asymmetrically positioned along the elongate body thereby positioning at least one of the energy providing feature and the distal end of the passageway against an inner wall of a carotid artery when the first inflatable holdfast and the second inflatable holdfast are inflated.

* * * * *